United States Patent [19]
Haupert, Jr.

[11] Patent Number: 5,716,937
[45] Date of Patent: Feb. 10, 1998

[54] METHOD FOR TREATING CARDIAC MALFUNCTION

[75] Inventor: Garner Haupert, Jr., Littleton, Mass.

[73] Assignee: The General Hospital Corporation, Charlestown, Mass.

[21] Appl. No.: 338,264

[22] Filed: Nov. 10, 1994

Related U.S. Application Data

[63] Continuation of Ser. No. 978,872, Nov. 19, 1992, abandoned, which is a continuation-in-part of Ser. No. 450,048, Dec. 13, 1989, abandoned.

[51] Int. Cl.$^6$ ............................................. A61K 31/70
[52] U.S. Cl. ............................................. 514/25; 536/5
[58] Field of Search ............................................. 536/5; 514/25

[56] References Cited

U.S. PATENT DOCUMENTS

| | | | |
|---|---|---|---|
| 4,551,426 | 11/1985 | Freytag et al. | 435/7 |
| 4,665,019 | 5/1987 | Hamlyn et al. | 435/21 |
| 4,780,314 | 10/1988 | Graves | 424/520 |
| 5,164,296 | 11/1992 | Blaustein et al. | 435/7.24 |
| 5,429,928 | 7/1995 | Blausten et al. | 435/7.24 |

FOREIGN PATENT DOCUMENTS

WO92/04047  3/1992  WIPO.

OTHER PUBLICATIONS

Hunter, Meredith Mudgett et al., "High–Affinity Monoclonal Antibodies to the Cardiac Glycoside, Digoxin," *The Journal of Immunology*, 129(3):1165–1172 (1982).

Carilli, Cynthia T. et al., "Hypothalamic Factor Inhibits the (Na,K)ATPase from the Extracellular Surface," *The Journal of Biological Chemistry*, 260(2):1027–1031 (1985).

Janssens, Stefan P. et al., "Hypothalamic $Na^{30}$, $K^{30}$–ATPase Inhibitor Constricts Pulmonary Arteries of Spontaneously Hypertensive Rats," *Journal of Cardiovascular Pharmacology*, 22(Suppl. 2):S42–S46 (1993).

Haupert, Garner T., Jr. and Sancho, Jose M., "Sodium transport inhibitor from bovine hypothalamus," *Proc. Natl. Acad. Sci. USA*, 76(9):4658–4660 (1979).

Haupert, Garner T., Jr. et al., "Hypothalamic sodium–transport inhibitor is a high–affinity reversible inhibitor of $Na^+$–$K^+$–ATPase," reprint from *American Physiological Society*:F919–F924 (1984).

Mirsalikhova, N.M. et al., "Some Features of the Inhibition of $Na^{30}$, $K^{30}$ –ATPase in Heart Muscle by Cardiotonic Glycosides," *Institute of Biochemistry and Institute of Chemistry of Plant Substances, Academy of Sciences and the Urbek SSR*, Tashkent, USSR, pp. 269–275.

Mudgett–Hunter, Meredith et al., "Binding and Structural Diversity Among High–Affinity Monoclonal Anti–Digoxin Antibodies," *Molecular Immunology*, 22(4):477–488 (1985).

Smith, Thomas W. et al., "Treatment of Life–Threatening Digitalis Intoxication with Digoxin–Specific Fab Antibody Fragments," *The New England Journal of Medicine*, 307(22):1357–131362 (1982).

Smith, Thomas W. et al., "Reversal of Advances Digoxin Intoxication with Fab Fragments of Digoxin–Specific Antibodies," *The New England Journal of Medicine*, 294(15):797–800 (19767).

Hallaq, Haifa A. and Haupert, Garner T., Jr., "Positive inotropic effects of the endogenous $Na^+$/$K^+$–transporting ATPase inhibitor from the hypothalamus," *Proc. Natl. Acad. Sci. USA*, 86:10080–10084 (1989).

Axelrod, Julius, "J. Methylation Reactions in the Formation and Metabolism of Catecholamines and Other Biogenic Amines," *Pharmacological Reviews*, 18(1), Part I:95–113 (1966).

Thomas, Richard et al., "Synthesis and Biological Activity of Semisynthetic Digitalis Analogs," *Journal of Pharmaceutical Sciences*, 63(11):1649–1683 (1974).

Hoffman, Brian F. and Bigger, J. Thomas, Jr. "Chapter 34 Digitalis and Allied Cardiac Glycosides," in *The Pharmacological Basics for Therapeutics* (NY: Pergamon Press), pp. 814–839 (1990).

Sergio Bova, et al., "Effects of an Endogenous Ouabainlike Compound on Heart and Aorta," *Hypertension* 17(6), Part 2 pp. 944–950, Jun. 1991.

W. Rodney Mathews et al., "Mass Spectral Characterization of an Endogenous Digitalislike Factor From Human Plasma," *Hypertension* 17(6), Part 2, pp. 930–935, Jun. 1991.

James H. Ludens et al., "Purification of an Endogenous Digitalislike Factor From Human Plasma for Structural Analysis," *Hypertension* 17(6) Part 2, pp. 923–929, Jun. 1991.

J.M. Hamlyn et al., "Identification and characterization of a ouabainlike compound from human plasma," *Proc. Natl. Acad. Sci. USA* 88:6259–6263, Jul. 1991.

Haupert, Jr.; in *The $Na^+$, $K^+$–Pump, Part B: Cellular Aspects*; Alan R. Liss, Inc., New York; 1988; pp. 297–320.

Harris et al., TIBTECH, 11: 42–44, 1993.

Waldmann, Science, 252: 1657–1662, 1991.

Foon, Cancer Res, 49: 1621–39, 1989.

Dermer, Biotechnology, 12: 320, 1994.

*Primary Examiner*—Elli Peselev
*Attorney, Agent, or Firm*—Hamilton, Brook, Smith & Reynolds, P.C.

[57] ABSTRACT

A method of treating cardiac malfunction by administering a positive inotropic effect-producing amount of Hypothalamic Inhibitory factor (HIF).

8 Claims, 15 Drawing Sheets

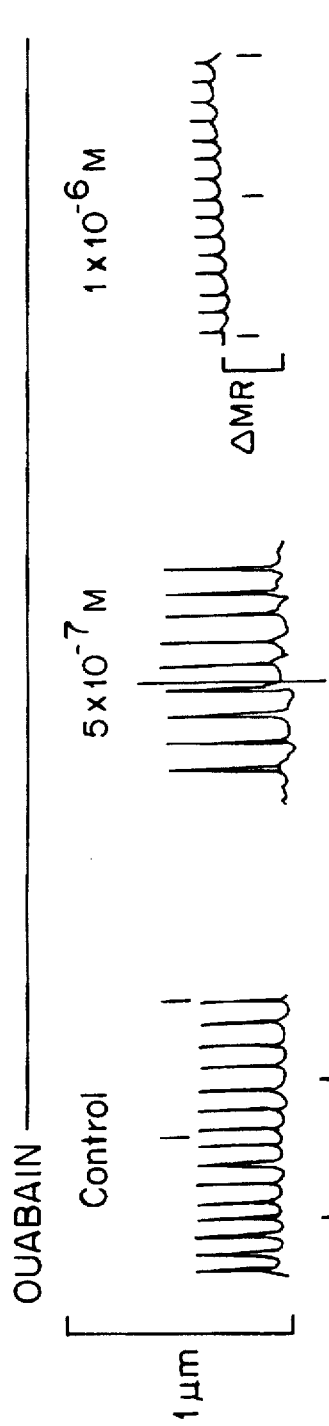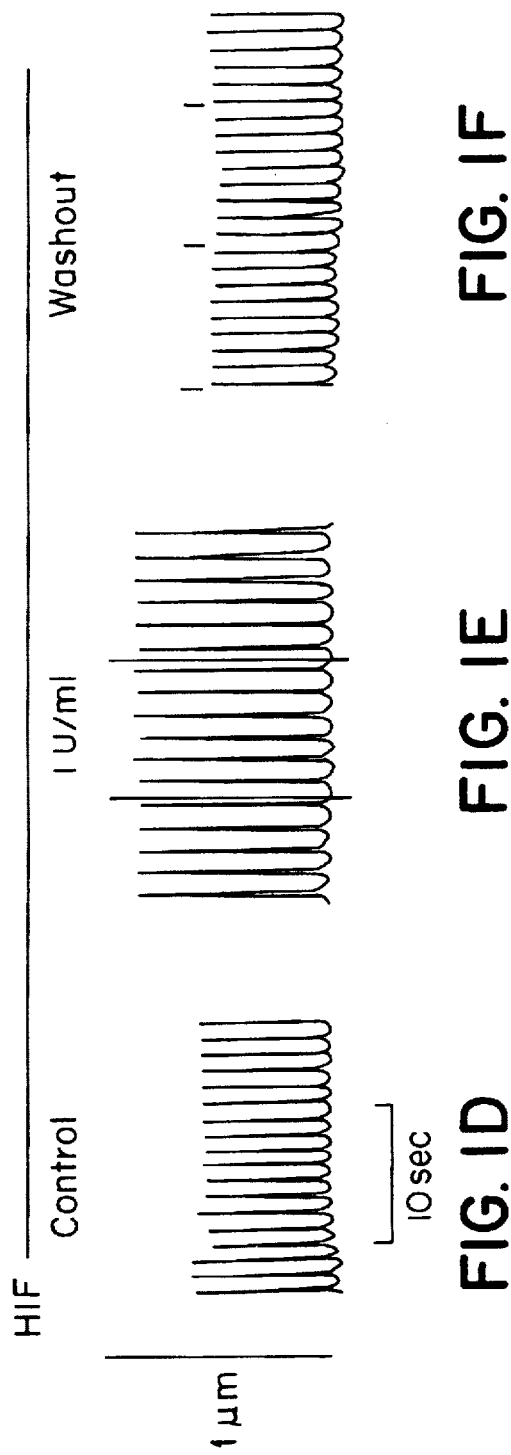

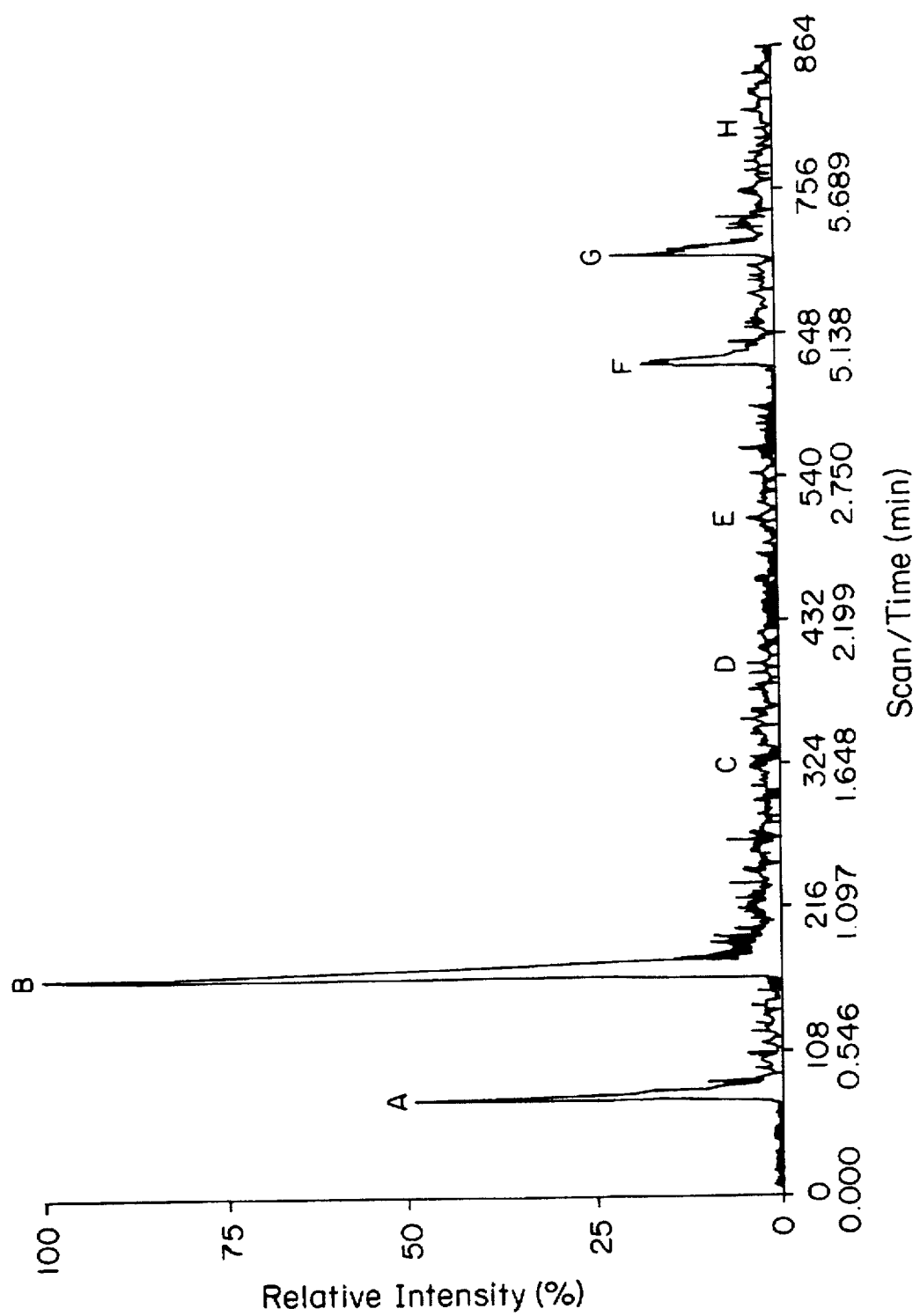

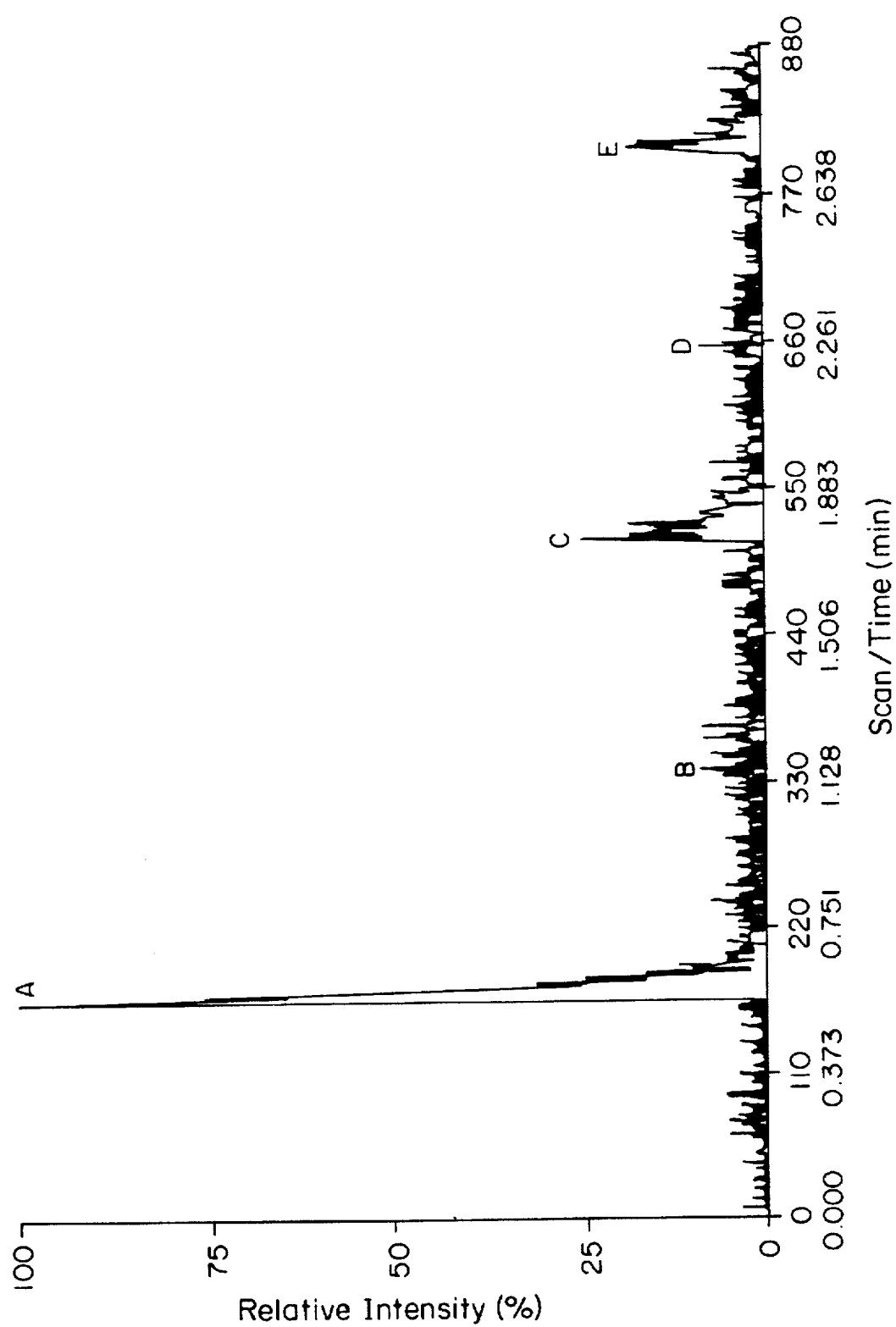

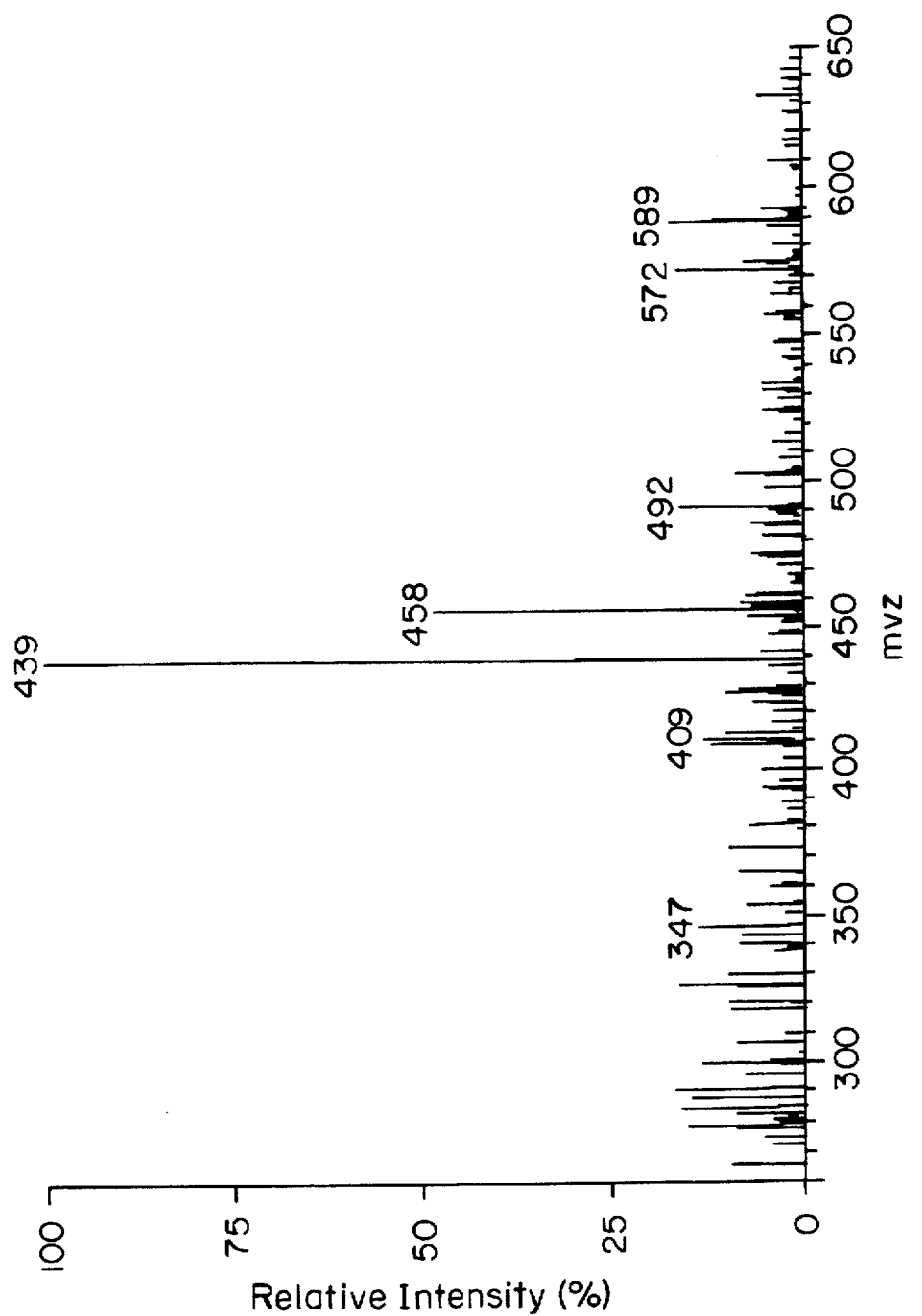

METHOD FOR TREATING CARDIAC MALFUNCTION

RELATED APPLICATION

This Application is a Continuation of U.S. application Ser. No. 07/978,872 filed Nov. 19, 1992, now abandoned, which is a Continuation-in-Part of U.S. application Ser. No. 07/450,048 filed Dec. 13, 1989 now abandoned.

GOVERNMENT FUNDING

This invention was made with Government support under Contract #1-K08HL00689 awarded by the National Institutes of Health. The government has certain rights in this invention.

BACKGROUND OF THE INVENTION

Digitalis, digoxin, ouabain and related substances are cardiac glycosides derived from plants. The main pharmacodynamic property of cardiac glycosides is the ability to increase the force of myocardial contraction in a dose-dependent manner (positive inotropic effect). The most probable explanation for the direct positive inotropic effect is the ability of cardiac glycosides to inhibit membrane-bound $Na^+$, $K^+$-activated adenosine triphosphatase ($Na^+$, $K^+$-ATPase) (Hoffman, B. F. and J. T. Bigger, Jr., "Digitalis and Allied Cardiac Glycosides" in *The Pharmacological Basis of Therapeutics*, eds. Goodman and Gilman, p. 732, (1980)). The hydrolysis of adenosine triphosphate (ATP) by this enzyme provides the energy for the sodium potassium pump.

Relatively little is known about the endogenous regulation of $Na^+$, $K^+$-ATPase. Catecholamines (Phillis, J. W., *Cell, Tissue and Organ Cultures in Neurobiology*, pp. 93–97 (1978); Horwitz, B. A., *Fed. proc.*, 38:2170–2176 (1979)), thyroid hormone (Smith, T. J. and I. S. Edelman, *Fed. Proc.*, 38:2150–2153 (1979)), aldosterone (Rossier, B. C., et al., *Science*, 12:483–487 (1987)), linoleic and linolenic acids (Bidard, J. N., et al., *Biochem. Biophys. Acta.*, 769:245 (1984); Tamura, M., et al., *J. Biol. Chem.*, 260:9672 (1985); and vanadium (Cantley, L. C., Jr., et al., *J. Biol. Chem.*, 243:7361–7368 (1978)) have all been linked to either direct or indirect effects on enzyme activity.

Many researchers have tried to isolate a specific endogenous inhibitor of plasma membrane $Na^+$, $K^+$-ATPase similar to digitalis or ouabain, but of mammalian origin, by measuring immunoreactivity in plasma, to the digoxin radioimmunoassay in situations where the inhibitor might be elevated. Klingsmueller et al. found digitalis like immunoreactivity in the urine of $Na^+$-loaded normal human subjects (Klingsmueller, et al., *Klin. Wochenschr.*, 60: 1249–1253 (1982)). Graves, S. W., et al. made a similar observation in the plasma of uremic subjects (Graves, S. W., et al., *Ann. Intern. Med.*, 99:604–608 (1983)).

The definitive structure of plasma, urinary or tissue inhibitor of $Na^+$, $K^+$-ATPase is not known (Haupert, G. T., Jr., in *The $Na^+K^+$-Pump, Part B: Cellular Aspects*; Skou, J. C., et al., Eds., p. 297–320 (1988)). Furthermore, the degree to which various candidate compounds are truly "digitalis-like" in either structure or function remains controversial, since even those substances characterized in the greatest biochemical detail manifest some differences with the cardiac glycosides, digitalis and ouabain (Carilli, C. T., et al., *J. Biol. Chem.*, 260: 1027–1031 (1985); Crabos, M., et al., *Eur. J. Biochem.*, 162:129 (1987); Tamura, M., et al., *Biochem.*, 27:4244–4253 (1988)).

For example, the digitalis-like factor (DLF) isolated by Graves cross-reacts with antidigoxin antibodies (Graves, S. W., U.S. Pat. No. 4,780,314)). However, DLF has never been shown to be a physiologic inhibitor, as would be expected of an endogenous regulator. By physiologic is meant an inhibitor that has a very high binding affinity for the enzyme; reversibly binds and inhibits; has high specificity for the membrane $Na^+$, $K^+$-ATPase; and is responsive to relevant stimuli.

Because of their positive inotropic effect, cardiac glycosides (e.g., digitalis and ouabain) are unrivaled in value for the treatment of heart failure. Cardiac glycosides are most frequently used therapeutically to increase the adequacy of the circulation in patients with congestive heart failure and to slow the ventricular rate in the presence of atrial fibrillation and flutter.

However, cardiac glycosides have narrow therapeutic indices and their use is frequently accompanied by toxic effects that can be severe or lethal. The most important toxic effects, in terms of risk to the patient, are those that involve the heart (e.g., abnormalities of cardiac rhythm and disturbances of atrio-ventricular conduction). Gastrointestinal disorders, neurological effects, anorexia, blurred vision, nausea and vomiting are other common cardiac glycoside-induced reactions.

SUMMARY OF THE INVENTION

This invention relates to Applicant's finding that Hypothalamic Inhibitory Factor, (HIF), has a positive inotropic effect on cardiac muscle cells. The invention further relates to Applicant's finding that HIF is a potent constrictor of pulmonary artery and aortic tissue. Thus, the invention comprises, in one embodiment, a method for producing a positive inotropic effect in a mammalian host by administering to said host a positive inotropic effect-producing amount of HIF.

HIF does not manifest the same toxicity profile as the cardiac glycosides. Therefore, therapy of cardiac malfunctions with HIF can be accomplished with less risk of toxicity to the patient.

This invention further relates to the findings that HIF can be administered therapeutically to treat cardiac glycoside intoxication, edematous disorders and hypotension. Also, HIF can be used to develop specific therapies to prevent hypertension.

BRIEF DESCRIPTION OF THE DRAWINGS

FIG. 1 is a graph produced by a phase contrast microscope video motion detector showing the effects of ouabain (upper panel) and HIF (lower panel) on cardiac myocyte contractility.

FIG. 7A represents tandem mass spectrometry analysis of HIF and ouabain.

FIG. 7B represents tandem mass spectrometry analysis of HIF and ouabain.

FIG. 9A shows HIF pentanaphthoate; FIG. 9B shows ouabain pentanaphthoate; FIG. 9C shows coinjection of HIF and ouabain pentanaphthoates.

FIG. 15A shows the full scan mass spectra of naringinase-hydrolysed HIF.

DETAILED DESCRIPTION OF THE INVENTION

Figure 2:
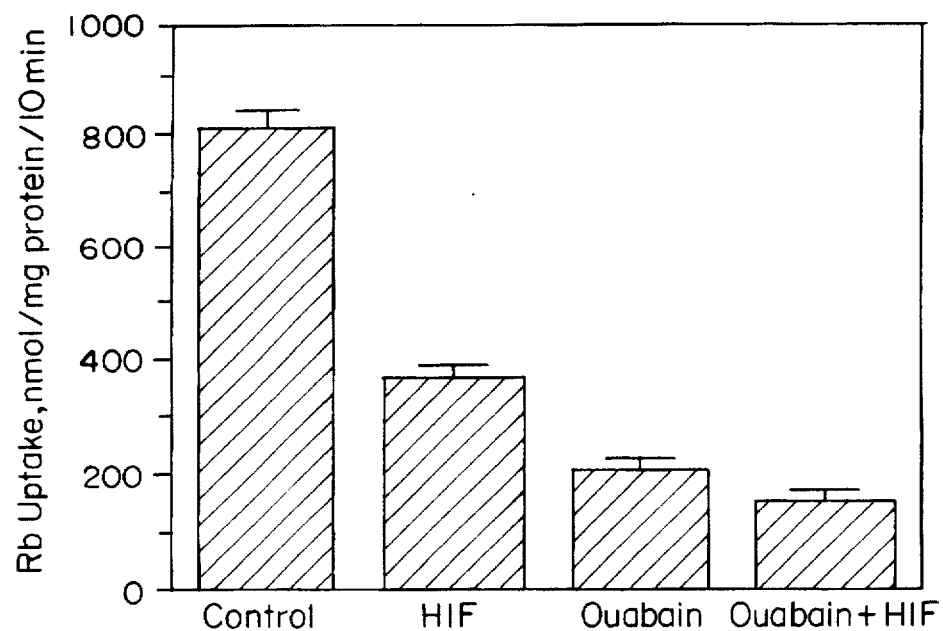
FIG. 2 is a graph plotting the inhibitory effects of HIF (2 units/ml) and ouabain (5 mM) or both on total $^{86}Rb^+$ uptake by neonatal rat cardiac myocytes.

A physiologic $Na^+$, $K^+$-ATPase regulator has been isolated from bovine hypothalamus and has been named hypothalamic inhibitory factor (HIF). (Haupert, G. T., Jr., et al., *Am. J. Physiol.*, 247:F919 (1984). Methods of isolating HIF are described in detail in Examples I and VII.

Using affinity chromatography and reversed phase HPLC, HIF has been purified to homogeneity and its structure characterized. HIF is shown herein to have the same molecular mass as ouabain (584 daltons) and to contain an L-rhamnose. In addition, chemical ionization studies show that elimination of the rhamnose produces a daughter ion of the same mass as the aglycone (genin) portion of ouabain. However, when acyl derivatives were prepared from authentic ouabain and purified HIF, the two compounds were shown to be structurally distinct as measured by their HPLC and circular dichroism profiles. These differences are consistent with the observed differences in pharmacologic effects between the two compounds (Cantiello, H. F., Chen, E., Ray, S. and Haupert, G. T. Jr. *Am. J. Physiol.* 255:F574–F580 (1988); Hallaq, H. A. and Haupert, G. T. Jr., *Proc. Natl. Acad. Sci. USA* 86: 10080–10084 (1989); Janssens, S. P., Kachoris, C., Parker, W. L., Hales, C. A. and Haupert, G. T. Jr. (in press) *J. Cardiovasc. Pharmacol.*; Anner, B. M., Rey, H. G., Moosmayer, M., Meszoely, L., and Haupert, G. T. Jr., *Am. J. Physiol.* 258: F144–F153 (1990)). HIF satisfies several essential biochemical criteria for a physiologic regulator of the $Na^+$ pump (Haupert, G. T., Jr. and J. M. Sancho, *Proc. Natl. Acad. Sci. USA*, 76:4658–4660 (1979)). HIF inhibits purified $Na^+$, $K^+$-ATPase reversibly and with high affinity ($K_i$=1.4 nM) (Haupert, G. T., Jr., et al., *Am. J. Physiol.*, 247:F919–F924 (1984)). In addition, its effects are specific (Carilli, C. T., et al., *J. Biol. Chem.*, 260:1027–1031 (1985)).

Purified Hypothalamic Inhibitory Factor (HIF) has now been found to have a positive inotropic effect on cardiac muscle cells (i.e., myocytes), as mentioned above. "Positive inotropic effect" means that the contractility of the cells is enhanced in a dose-dependent manner.

A positive inotropic effect-producing amount of HIF can be administered to a "mammalian host" (e.g., a human) to treat cardiac malfunction (e.g., congestive heart failure, paroxysmal atrial tachycardia, atrial fibrillation and flutter). Administration can be either enteral (i.e., oral) or parenteral (e.g., via intravenous, subcutaneous or intramuscular injection). In addition, as HIF does not manifest the same toxicity profile as the cardiac glycosides, therapy of cardiac malfunctions with HIF can be accomplished with less risk of toxicity to the patient.

FIG. 1 is a graph showing the positive inotropic effects on myocytes exposed to 1 unit/ml of HIF in comparison to $5 \times 10^{-7}$ M ouabain; and in comparison to the toxic effects on myocytes exposed to $1 \times 10^{-6}$ M ouabain. In this experiment, one unit of HIF is defined as the amount necessary to inhibit 1 µg of highly purified $Na^+$, $K^+$-ATPase by 50% under standard assay conditions at 37° C. (Haupert, G. T., et al., *Am. J. Physiol.*, 247:F919–F924 (1984)). See Example VI.B. for a more detailed discussion of the definition of HIF units of activity. The protocol for the contractility experiments is set forth in Example III C.

In general, the amplitude of contraction (i.e., degree of positive inotropy) was measured in single, beating myocytes as the amplitude of systolic motion (ASM) using a phase contrast video motion detector system. The same detector system was used to measure toxicity, which is evidenced as a decrease in ASM, a change in the position of maximal relaxation (MR), and an increase in beating frequency.

FIG. 1B shows that $5 \times 10^{-7}$ M ouabain, a maximally inotropic but non-toxic dose in these cells, increases amplitude of systolic motion (ASM) by 41% and caused a decrease in beating frequency compared to the same cells in the control period (FIG. 1A). There was no change in the position of maximal relaxation (MR), indicating "therapeutic range" but non-toxic effects.

FIG. 1C shows that a 1 µM concentration of ouabain causes a decrease in ASM, an elevation in the position of MR, and an increase in beating frequency, all indicating "toxic range" effects of this only 2-fold higher dose on the contracting myocytes, reflecting the narrow therapeutic index of cardiac glycosides.

FIG. 1E shows that 1 unit/ml HIF causes a 37±3% increase in ASM compared to control (FIG. 1D), with a decrease in beating frequency and no change in the position of MR. Therefore, 1 unit/ml is within the therapeutic range, but exhibits no toxic effects.

FIG. 1F shows the results following a 1 minute "washout", during which the same cell was perfused with HIF-free buffer. ASM and beating frequency returned to control levels indicating rapid reversibility of the positive inotropic effects caused by HIF.

HIF effects are more readily reversible than those of ouabain, since a 5 minute washout period in ouabain-treated neonatal rat myocytes is required to return enhanced contractility to control levels (Werdan, K., et al., *Biochem. Pharmacol.*, 33:1873–1886 (1984)).

In addition to its use in treating cardiac malfunction, a pharmaceutical composition of HIF can be administered (e.g., enterally or parenterally) to treat patients with serious or life-threatening cardiac glycoside intoxication. Currently, cardiac glycoside intoxication is treated either generally by administering potassium or antiarrhythmic drugs to the patient, or specifically by administering antibody fragments to specific cardiac glycoside preparations. Patients with severe toxicity may be unresponsive to general methods of treatment. In addition, although treatment with antibody fragments does neutralize cardiac glycosides in circulation, the antibodies may not effect cardiac glycosides that are bound to cardiac tissue. Furthermore, because antibodies are proteins, they are administered intravenously and can cause allergic reactions.

In contrast, HIF not only blocks circulating cardiac glycosides from binding to the $Na^+$, $K^+$-ATPase, but also elutes or "chases" previously bound cardiac glycoside from $Na^+$, $K^+$-ATPase, presumably by competing with or interfering with the cardiac glycoside binding site. "Chase" experiments were performed using an assay system whereby purified $Na^+$, $K^+$-ATPase is reconstituted into liposomes (Anner, B. M. and M. Moosmayer, *Biochem. Biophys. Res. Commun.*, 129:102–108 (1985)). The detailed protocol for these experiments is set forth in Example IV, and results presented in Table 3. In general, liposomes containing functional $Na^+$, $K^+$-ATPase molecules were incubated with $^3$H-ouabain which permits measurement of specific ouabain binding to its binding site on the $Na^+$, $K^+$-ATPase. The liposome-$Na^+$, $K^+$-ATPase-ouabain complex was then exposed to varying doses of HIF for 10 minutes at 25° C. The bound $^3$H-ouabain was eluted from the $Na^+$, $K^+$-ATPase by HIF in a dose-dependent manner, with complete elution of the bound ouabain at an HIF concentration of 0.5 units per 2.5 microliters liposomes.

Thus, HIF is not only able to prevent digitalis compounds from binding to the $Na^+$, $K^+$-ATPase, but, as shown by these experiments, is able to displace cardiac glycoside already bound to the $Na^+$, $K^+$-ATPase. Therefore, treatment of cardiac glycoside intoxication with HIF could serve as a highly specific therapy to rapidly reverse the toxic effects on the heart. In addition, as a non-peptide, oral administration of HIF is possible.

HIF can also be administered (e.g., enterally or parenterally) to treat blood pressure abnormalities. Studies have shown that excess of endogenous circulating inhibitor of $Na^+$, $K^+$-ATPase may be responsible for essential hypertension in some or many patients. (DeWardener, H. E. and G. W. MacGregor, *Kidney Int.*, 18:1–9 (1980)). Presumably, the increased intracellular calcium ion concentration resulting from the binding of an inhibitor to $Na^+$, $K^+$-ATPase produces blood vessel constriction and hypertension (Blaustein, M. P., *Am. J. Physiol.*, 232:C165–C173 (1977)).

Experiments were conducted to determine the vasoconstrictive properties of HIF. The protocol for these experiments is described in greater detail in Example V. In general, Sprague-Dawley rats were anesthetized and the abdominal aorta surgically removed. 2 mm vascular rings were attached to a force transducer and bathed in buffer, and tension adjusted to 1.5 g. Tissue viability was documented and vasoconstrictive responses calibrated using known vasoconstrictors such as potassium chloride and norepinephrine. Blood vessels thus prepared were then tested with varying doses of HIF.

HIF produced potent, reversible vasoconstriction of the vessels, and these responses were dose dependent. Vessels remained completely viable after exposure to HIF, documenting absence of toxic effects. Maximum vasoconstrictive responses were similar to those produced by the known vasoconstrictor substances used as standards. Hypotension, abnormally low blood pressure, can be caused by low cardiac output, inadequate vascular constriction, or both occurring simultaneously. Since HIF has been demonstrated to both increase the strength of cardiac cell contraction and promote blood vessel constriction, its administration in therapeutic amounts would be an effective treatment for hypotension.

Experiments were further conducted to determine the vasoconstrictive effects of HIF on Sprague-Dawley rat and spontaneously hypertension rat (SHR) pulmonary artery tissue and abdominal aorta tissue. The protocol for these experiments is described in greater detail in Example VI. In general, Sprague-Dawley rats or SHR were anesthetized and the pulmonary artery (PA) and abdominal aorta (AO) surgically removed. 2–3 mm vascular rings were cut from these tissues, attached to a force transducer and bathed in buffer. The tension in the transducer was adjusted to 1.5 g. Tissue viability was documented and vasoconstrictive responses calibrated using known vasoconstrictors such as potassium chloride and norepinephrine. The response to 20 U (~4 nM) HIF of blood vessels thus prepared were then compared.

HIF constricted PA rings of hypertensive rats to a significantly greater extent than PA rings of normotensive rats. However, this difference was not observed in abdominal aortic rings. In addition, no significant difference in HIF-induced contractions was observed between aortic and pulmonary artery rings in normotensive animals, but in hypertensive animals the effect of HIF was significantly greater in the pulmonary artery rings compared to the aortic rings. In all cases, contraction was abolished by phentolamine, but was unaffected by calcium channel blockade using verpamil. In addition, HIF-induced tension development required external $Ca^{2+}$.

HIF can also be used to develop specific therapies to prevent excessive vasoconstriction and resulting hypertension. Such therapies would include but not be limited to: (1) Administering antibodies to HIF for passive immunizations; (2) administering immunogenic forms of for active immunity against hypertension; and (3) administering analogues of HIF which could prevent or modulate binding of native HIF to and action on the vascular cell $Na^+$, $K^+$-ATPase.

In addition, by potently inhibiting the $Na^+$, $K^+$-ATPase activity of renal tubular cells and thereby promoting sodium excretion, a pharmaceutical composition of HIF can be used as a natural diuretic, to promote excretion of excess salt and water by the kidneys in patients suffering from such common clinical conditions as congestive heart failure, cirrhosis of the liver, and nephrotic syndrome. Because of the specific inhibitory effect that HIF has on $Na^+$, $K^+$-ATPase, diuretic therapy with HIF can be accomplished without the side effects (e.g., impotence, rashes, blood lipid abnormalities) which commonly occur with existing diuretic drugs.

This invention is illustrated further by the following examples, which are not to be construed as limiting in any way.

EXEMPLIFICATION

I. Preparation of HIF

The $Na^+$, $K^+$-ATPase inhibitor was prepared from bovine hypothalamus as previously described (Carilli, C. T., et al., J. Biol. Chem., 260:1027–1031 (1985)). Hypothalami collected fresh and frozen immediately on dry ice were thawed, homogenized and extracted in methanol:water (4:1, v:v). Methanol was removed by flash evaporation, and lipids removed by extraction of the remaining aqueous phase with petroleum ether and chloroform. Initial separation of HIF was carried out using lipophilic gel chromatography (Carilli, C. T., et al., J. Biol. Chem., 260:1027–1031 (1985)). Further purification was accomplished using successive cation and anion exchange chromatographies. Approximately 100 units HIF from the lipophilic gel chromatographies was dissolved in 10 ml doubly distilled water (ddH$_2$O), applied to a small column containing 10 ml of sulfonic acid cation exchange resin in the protonated form (Amersham, IR 120), and eluted with ddH$_2$O at 1 ml/minute. The effluent was collected, lyophilized, the residue taken up in 1 ml ddH$_2$O and applied to a column containing 1.5 ml Amberlite IR 958 (Schweizerhall, Inc.) in the bicarbonate form. The column was eluted successively with two bed volumes ddH$_2$O. An aliquot of the eluate was assayed for specific Na$^+$, K$^+$-ATPase inhibitory activity (HIF) in a coupled-enzyme assay (Haupert, G. T., et al., Am. J. Physiol., 247:F919–F924 (1984)) and a human erythrocyte $^{86}$Rb$^+$ uptake assay (Carilli, C. T., et al., J. Biol. Chem., 260:1027–1031 (1985)) to determine the concentration of HIF activity. The cation exchange step successfully removed small amounts of gamma amino benzoic acid, serine, threonine and glutamic acid, and the anion exchange step, trace amounts of lactate, all of which had been detected by mass spectroscopic analysis of active fractions following the lipophilic gel chromatographies. Recovery of HIF was quantitative following the ion-exchange steps. HIF following the above procedures is free of vanadate (emission spectroscopy), NH$_4$ ion (reductive amination, Sigma kit 170-A), and free fatty acids and lysophospholipids (gas chromatography-mass spectroscopy) which have been shown to interfere in pertinent bioassays.

II. Preparation of Cardiac Cells

Myocardial cells were isolated from ventrical fragments of the hearts of 1-day old Sprague-Dawley rats by serial trypsinizations in a Ca$^{2+}$ and Mg$^{2+}$-free Hanks Buffered Salt Solution (HBSS) as previously described (Yagev, S., et al., In Vitro, 20:893–898 (1984)). Trypsinized cells were decanted into HamF10 medium containing 20% serum and antibiotics and centrifuged at 1000 r.p.m. for 10 minutes. The cell pellet was resuspended in HamF10 medium containing fetal calf serum and 10% horse serum with 0.1% penicillin-streptomycin, and diluted to a concentration of 5×10$^5$ cells/ml. For measurements of cytosolic free calcium concentration ([Ca$^{2+}$]i), the cells were plated on rectangular glass coverslips (13×30 mm) and for measurements of cell contractility, plated on circular glass coverslips (12 mm), and both types of coverslips placed inside petri dishes. For measurements of $^{86}$Rb$^+$ uptake cells were plated in petri dishes (1–1.5×10$^6$ cells/35 mm dish). All cultures were incubated in humidified 5% CO$_2$, 95% air at 37° C. Confluent monolayers in which an estimated 80% of cells exhibited spontaneous synchronous contractions developed by three days, at which time experiments were performed.

III. Physiologic Effects of HIF on Cardiac Cells

A. $^{86}$Rb$^+$ Influx Measurements

Na$^+$ pump activity was estimated in the cultured cardiac cells as the difference in $^{86}$Rb$^+$ uptake observed in the absence and presence of 5 mM ouabain, following the method of Panet et al. (Panet, R., et al., J. Memb. Biol., 70:165–169 (1982)). To insure saturation binding, myocytes were preincubated for 20 minutes with HIF (2 unit/ml) or ouabain (5 mM) or both prior to addition of $^{86}$Rb$^+$ to run the 10 minute flux. Myocyte monolayers were washed with HEPES buffer solution (final concentrations, mM: NaCl 150, RbCl 5, HEPES-Tris 10 (pH7.0), CaCl$_2$ 1, MgCl$_2$ 5, glucose 10), and the uptake initiated by covering over with 0.5 ml of same solution pre-warmed to 37° C. and containing 2 µCi $^{86}$RbCl. Incubations were continued for up to 10 minutes (period of linear uptake of the isotope) (Heller, M., et al., Biochem. Biophys. Acta, 939:595–602 (1988)), and the uptake terminated by aspiration of the reaction mixture followed by two rapid rinses with 3 ml ice-cold MgCl$_2$ (125 mM) and two with 5 ml ice-cold NaCl (165 mM). The cells were lysed with 0.6 ml of 0.1N NaOH containing 0.1% (w/v) sodium dodecylsulfate, and the radioactivity counted in Instagel (Packard) scintillation medium.

FIG. 2 illustrates the inhibitory effects of HIF (2 units/ml) and ouabain (5 mM) or both on total $^{86}$Rb$^+$ uptake by neonatal rat cardiac myocytes. Na$^+$ pump mediated uptake (600 nmol/mg protein/10 minutes) is calculated as the difference in total uptake, and uptake in the presence of 5 mM ouabain.

Ouabain (5 mM) decreased uptake from control levels of 810 nmol/mg protein to 210 nmol/mg (74%), while HIF (2 units/ml) decreased the uptake from control levels to 377 nmol/mg (54%). The combination of ouabain plus HIF was not additive, indicating that HIF inhibitory effects are specific for K$^+$ transport through the Na$^+$, K$^+$-ATPase, as has been previously shown for human erythrocytes (Carilli, C. T., et al., J. Biol. Chem., 260:1027–1031 (1985)) and renal tubular cells (Cantiello, H. F., et al., Am. J. Physiol., 255:F574–F580 (1988)). HIF (2 unit/ml) thus inhibited ouabain-sensitive K$^+$ transport in myocytes by 74%.

The concentration dependence of HIF inhibition was determined by preincubating cells with HIF at 0.5 units/ml, 0.8 units/ml, 1 unit/ml, 2 units/ml and 4 units/ml concentration for 20 minutes. $^{86}$RbCl (2 µCi/well) was then added to run the flux.

Figure 3:
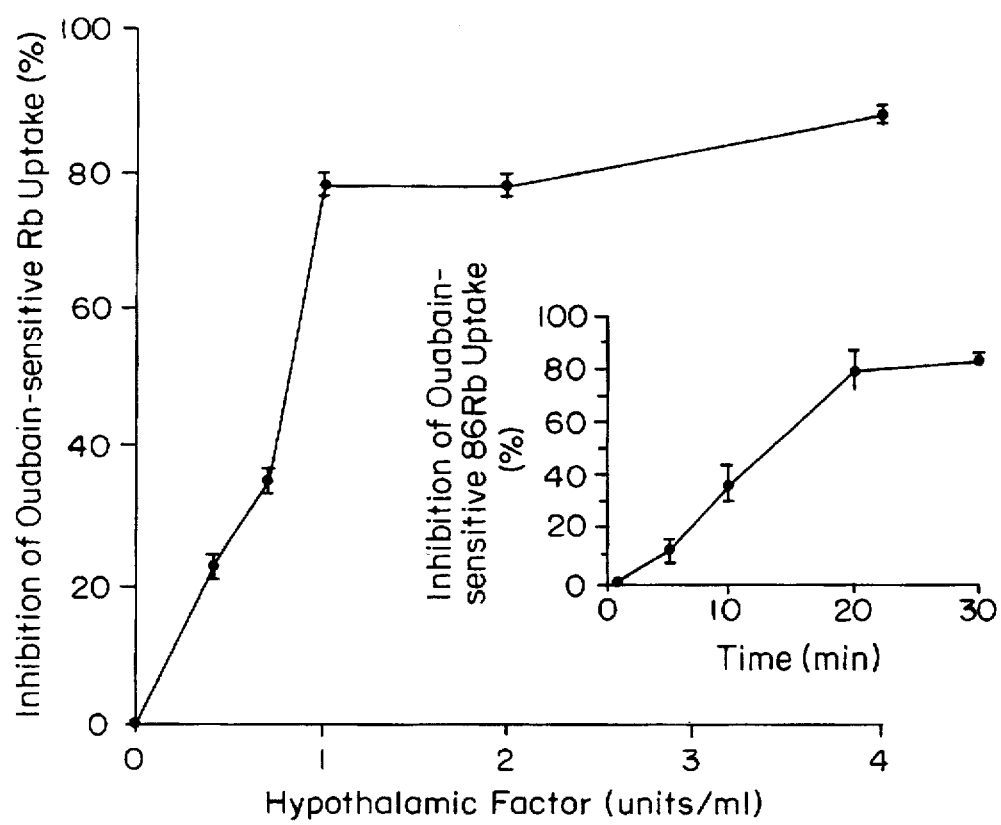
FIG. 3 is a graph plotting the inhibitory effects of increasing doses of HIF on ouabain-sensitive $^{86}Rb^+$ uptake (sodium pump activity) in myocytes.

FIG. 3 shows the concentration dependence of HIF inhibition of ouabain-sensitive RB$^+$ uptake (a specific measure of Na$^+$, K$^+$-ATPase activity) in neonatal rat cardiac myocytes. Values are mean ±SEM for n=4 determinations at each concentration. HIF-mediated Na$^+$ pump inhibition is dose-dependent and related to the amount of time that the myocytes are exposed to the inhibitor. Ninety percent of Na$^+$ pump activity in the neonatal rat myocytes is inhibited by the maximal dose of HIF (4 units/ml). FIG. 3 (inset) illustrates the inhibition of active K$^+$ transport as a function of the time that myocytes are exposed to HIF (2 units/ml). Maximal inhibitory effects (i.e., inhibition of myocyte Na$^+$, K$^+$-ATPase activity by about 90%) required 20–30 minutes preincubation with HIF.

However, significant pump inhibition also occurred after shorter exposures to HIF. The ID$_{50}$ for pump inhibition in neonatal rat myocytes occurs at an HIF concentration of about 0.5 units/ml. This is approximately 30 fold less than that for cultured porcine renal tubular cells (Cantiello, H. F., et al., J. Physiol., 255:F574–F580 (1988)), therefore suggesting that neonatal rat myocytes have a relatively higher affinity for HIF.

B. Measurement of Cytosolic Free Ca$^{2+}$ ([Ca$^{2+}$])

Changes in [Ca$^{2+}$]i were detected using the fluorescent probe, fura-2 (Grynkiewicz, G., et al., J. Biol. Chem., 260:3440–3450 (1985)). Rectangular glass coverslips with attached myocytes were placed in buffered salt solution (BSS, containing in mM: NaCl 140, KCl 5, $CaCl_2$ 1, $MgCl_2$ 1, glucose 10, $Na_2HPO_4$ 1, Hepes-Tris 10 (pH 7.4) to which was added 5 μM fura-2/AM, and incubated for 1 hour in humidified 5% $CO_2$-95% air at 37° C. Additional loading medium was added and incubation continued for 15 minutes to complete the hydrolysis of fura-2/AM. The cells were washed and incubated an additional 30 minutes in BSS. Coverslips with loaded myocytes were inserted into a thermostrated (37° C.) cuvette containing 2 ml BSS and various additions of HIF or ouabain as indicated. The fluorescence was continuously recorded using a PTI DeltaScan 1 spectrofluorometer. Dual excitation wavelengths alternated rapidly (60 Hz) between 340 nm and 380 nm. emission wavelength 505 nm. Values of $[Ca^{2+}]i$ were calculated from the ratio $R=F_{340}/F_{380}$ using the formula: $[Ca^{2+}]i=K_d B (R-R_{min})/(R_{max}-R)$, where $K_d$ is 225 nM. $R_{max}$ and $R_{min}$ were determined in separate experiments using digitonin to equilibrate $[Ca^{2+}]i$ with ambient $[Ca^{2+}]$ ($R_{max}$), and addition of $MnCl_2$ (0.1 mM) and EGTA (1 mM) ($R_{min}$). Background auto-fluorescence was measured in unloaded cells and subtracted from all measurements.

Figure 4:
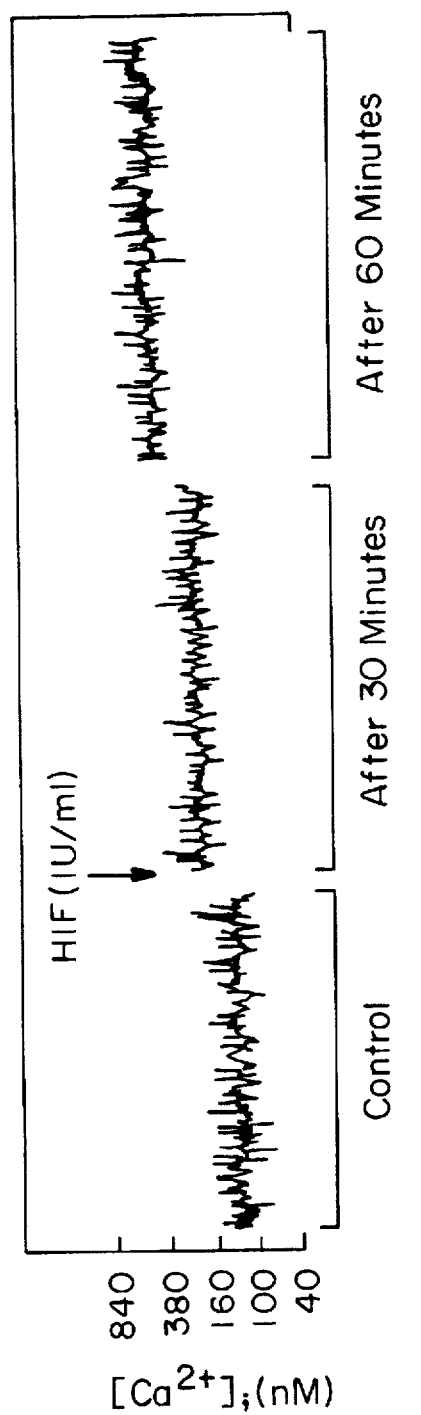
FIG. 4 is a fluorescence signal showing the effect of HIF (1 unit/ml) on cytosolic free $Ca^{+2}$ content in cultured cardiac myocytes exposed for 30 and 60 minutes.

FIG. 4 shows the effect of HIF (1 unit/ml) on cytosolic free calcium ion ($[Ca^{2+}]i$) content in cultured cardiac myocytes. Fluorescence of fura-2 loaded myocytes incubated in Buffered Salt Solution (BSS) was recorded continuously. Control value (138 nM) is for cells in BSS prior to addition of HIF (arrow). Recordings are shown after 30 minutes and 60 minutes exposure to HIF. Cytosolic free $Ca^{2+}$ concentrations increased from a baseline of 138 nM to 250 nM and 432 nM after 30 and 60 minutes exposure to HIF, respectively.

The onset of change in $[Ca^{2+}]i$ caused by HIF occurred within 15 minutes, reached a new steady state concentration by 60 minutes, and remained stable at this level for at least 2 hours.

The biochemical events underlying cardiac glycoside toxicity and the narrow therapeutic index characteristic of these drugs is incompletely understood, although excessive intracellular free $Ca^{2+}$ secondary to persistently elevated intracellular $Na^+$ associated with tonic pump inhibition has been postulated as having a central role (Tsien, R. W. and B. U. Carpenter, Fed. Proc. Fed. Am. Soc. Exp. Biol., 37:2127-2131 (1978)).

Table 1 shows increases in steady-state $[Ca^{2+}]i$ induced by various doses of HIF. A dose-response relationship was found with 0.5 unit/ml HIF increasing $[Ca^{2+}]i$ in the myocytes to a level (303±15 nM) similar to that caused by 1 μM ouabain (287±15 nM) under the same experimental conditions. HIF (1 unit/ml) raised $[Ca^{2+}]i$ to a level significantly greater than that induced by 1 μM ouabain.

TABLE 1

Changes in steady-state cytosolic free $Ca^{2+}$ concentrations ($[Ca^{2+}]i$) in cardiac myocytes treated with ouabain or various concentrations of HIF*

| | | | HIF (units/ml) | | |
|---|---|---|---|---|---|
| Condition | Control | Ouabain $10^{-6}$M | 0.25 | 0.5 | 1.0 |
| $[Ca^{2+}]i$(nM) | 138 ± 3 | 287 ± 15 | 197 ± 9 | 303 ± 15 | 432 ± 18 |

*Values are mean ± SEM; n = 3 determinations at each concentration

While 1 μM ouabain raises the intracellular concentration of $Ca^{2+}$ to 287±15 nM, and causes clear toxicity (FIG. 1C), 1 unit/ml of HIF raises the intracellular concentration of $Ca^{2+}$ in the same cells to a much higher level, 432±18 nM, but is accompanied by a stable, maximal inotropic effect with no sign of toxicity (FIG. 1E).

C. Measurements of Myocyte Contractility

Contractility, determined as amplitude of systolic cell motion (ASM), and beating frequency were measured in individual cells using a phase contrast microscope video motion detector system according to the method of Barry, et al., (Barry, W. H., et al., Circ. Res., 56:231-241 (1985)). A glass coverslip with attached cultured myocytes was placed in a chamber provided with inlet and exit ports for medium perfusion. The chamber was enclosed in a Lucite box at 37° C. and placed on the stage of an inverted phase contrast microscope. The cells were covered with 1 ml medium containing HIF or ouabain. During continuous perfusion, medium bathing a cell in the center of a coverslip exchanged with a time constant of 15 seconds at a flow rate of 0.96 ml/minute. Image was magnified using a 40× objective, and motion monitored by a low-light-level TV camera attached to the microscope and calibrated with 262 raster lines. The motion detector monitors a selected raster line segment and provides new position data every 16 msec for an image border of a microsphere within the cell layer moving along the raster line. The analog voltage output from the motion detector is filtered at low pass filter and calibrated to indicate actual μm of motion, and the derivative is obtained electronically and recorded as velocity of motion in μm/sec. Rate, amplitude and velocity of contraction remained stable for several hours during control perfusions. The changes in contractility induced by ouabain or HIF were calculated in comparison with the contractility of the same cells before addition of ouabain or HIF.

Table 2 summarizes changes in ASM and beating frequency as a function of various doses of HIF. Increasing concentrations of HIF caused progressive increase in ASM and decrease in beating rate. Maximal increase in ASM occurred at an HIF concentration of about 0.5 units/ml (39±6%), a level equal to the maximal, non-toxic dose of ouabain ($5×10^{-7}$M)

TABLE 2

Effects on amplitude of systolic motion (ASM) and beating rate in cardiac myocytes by various concentrations of HIF, and ouabain (Ou)*

| | HIF (units/ml) | | | | | Ou (M) |
|---|---|---|---|---|---|---|
| | 0.2 | 0.25 | 0.33 | 0.5 | 1.0 | $5 × 10^{-7}$ |
| ASM, % increase | 15 ± 2 | 22 ± 1 | 32 ± 9 | 39 ± 6 | 37 ± 3 | 41 ± 3 |
| Rate, % decrease | 12 ± 1 | 15 ± 1 | 25 ± 7 | 40 ± 2 | 49 ± 6 | 23 ± 2 |

*Values are mean ± SEM; n = 3 for each concentration

IV. HIF Ability to Displace Cardiac Glycosides from Their Binding Site on the $Na^+$, $K^+$-ATPase "Chase" experiments were performed using an assay system whereby purified $Na^+$, $K^+$-ATPase is reconstituted into phosphatidylcholine liposomes. ATP-filled liposomes containing dispersed, randomly oriented $Na^+$, $K^+$-ATPase molecules were prepared by the cholate-dialysis method according to Anner (Anner, B. M. and M. Moosmayer, Biophys. Res. Commun. 129:102-108 (1985)). Using this miniaturized, two-sided test system Applicant has also shown that $Na^+$, $K^+$-ATPase inhibition by a single dose of 0.1 U HIF (approximately 75 fmol), and the membrane permeation of 1.0 U HIF (approximately 750 fmol) became measurable, and that an estimation of the minimal number of HIF molecules per unit could be made (Anner, B. M., Rey, H. G., Moosmayer, M., Meszoely, L. and Haupert, G. T. Jr., *Am. J. Physiol.* 228:F144–F153 (1990)). Despite testing of numerous substances including other proposed endogenous $Na^+$, $K^+$-ATPase inhibitors, HIF is the only compound (besides the cardiac glycosides themselves) tested thus far in the purified system that displays such striking transport inhibition.

For "chase" experiments liposomes containing functional $Na^+$, $K^+$-ATPase molecules were incubated for 10 minutes at 25° C. with $^3$H-ouabain (10 µM), following which HIF was added in various doses and the incubation continued for 10 minutes at 25° C. Reactions were quenched by addition of 125 µl ice-cold stop solution, and the samples applied and eluted through (0° C.) a 20-cm Sephadex G-50 medium column which permits separation of bound from free $^3$H-ouabain. Bound $^3$H-ouabain was eluted from the $Na^+$, $K^+$-ATPase by HIF in a dose-dependent manner as shown in Table 3.

TABLE 3

Elution of $^3$H-ouabain bound to 2.5 µl $Na^+$, $K^+$-ATPase liposomes by various doses of HIF.

|  | –HIF | +HIF (units/ 2.5 µl liposomes) | | |
|---|---|---|---|---|
|  |  | 0.125 | 0.25 | 0.5 |
| $^3$H-ouabain bound (cpm) | 2902 | 178 | 111 | 45 |
| $^3$H-ouabain eluted (%) | — | 94.0 | 96.2 | 98.5 |

V. Vasoconstrictive Properties of the Hypothalamic $Na^+$, $K^+$-ATPase Inhibitor: The Effects of HIF on Vasoconstriction of Sprague-Dawley Rat Abdominal Aorta Rings Sprague-Dawley rats weighing 250–350 grams were anesthetized with pentobarbital intraperitoneally, the abdominal aorta rapidly excised and dissected free of all loose connective tissue in cold Krebs-Henseleit bicarbonate buffer of the following composition, mM: NaCl, 118.3; KCl, 4.7; $MgSo_4$, 1.2; $KH_2PO_4$, 1.2; $CaCl_2$, 2.5; $NaHCO_3$, 25.0; Na-EDTA, 0.016; and glucose, 11.1. 2–3 mm (length) vascular rings were excised, attached to a force transducer and bathed in a water jacketed (37° C.) organ chamber containing 5 ml of the above buffer gassed with 95% $O_2$ and 5% $CO_2$. Isotonic force measurements were obtained with a Grass force displacement transducer attached to a Grass 79D polygraph DC amplifier, and recorded with a two-channel Kipp Zonen recorder. Calibration studies revealed that aortic rings placed under 1.5 g tension generated a maximal contractile response after KCl depolarization, and all rings were therefore equilibrated under 1.5 g tension prior to starting experiments. Tissue viability for individual experiments was documented using known vasoconstrictors such as potassium chloride and norepinephrine. Blood vessels thus prepared were then tested with varying doses of HIF, and the magnitude of response compared with KCl-induced contractions. HIF produced potent, reversible vasoconstrictions of the vessels, and these responses were dose dependent as shown in Table 4.

TABLE 4

Effects on vascular tension in rat abdominal aortic rings by various concentrations of HIF, and KCl, shown as increase above resting tension of 1.5 g

|  | Change in Tension in Rat Aorta | | | | KCl (mM) |
|---|---|---|---|---|---|
|  | HIF (units/ml) | | | |  |
|  | 0.1 | 0.1 | 0.4 | 0.8 | 20 |
| % increase | 2 | 5 | 12 | 26 | 20 |

Vessels remained completely viable after exposure to HIF as judged by preservation of KCl responses following washout of HIF; documenting absence of toxic effects. Maximum vasoconstrictive responses were similar to those produced by the membrane depolarizing dose of KCl. These studies confirm that HIF is a potent vasoconstrictive substance, compatible with its proposed role in regulation of vascular tone and potential role in the pathogenesis of hypertensive disease.

VI. Vasoconstrictive Properties of the Hypothalamic $Na^+$, $K^+$-ATPase Inhibitor: The Effects of HIF of Vasoconstriction of Sprague-Dawley Rat and Spontaneously Hypertensive Rat Pulmonary Artery Rings and Abdominal Aorta Rings Spontaneously hypertensive rats show a moderate though significant degree of pulmonary hypertension which is not secondary to the systemic hypertension (Janssens, S. P., Thompson, T. B., Spence, C. R., Hales, C. A., *Am Rev Resp Dis* 143:A187 (1991)). In order to determine whether specific HIF sensitivity of the pulmonary vessels might be involved, the following experiments were conducted to compare the contractile responses of isolated pulmonary artery vessels (PA) from spontaneously hypertensive rats, SHR, and normotensive Sprague-Dawley rats. The results herein reported demonstrate that HIF is a potent vasoconstrictor of pulmonary arteries, and that this effect is significantly greater in spontaneously hypertensive rats than in normotensive Sprague-Dawley rats. HIF appears to act by modulating the $Na^+$, $K^+$-ATPase-adrenergic neuroeffector interaction at the neuromuscular junction.

A. Preparation and Mounting Of PA and Abdominal Aortic Rings

Adult male Sprague-Dawley (SD) and Spontaneously Hypertensive rats (SHR)(10–12 weeks, 300–400 g) were anesthetized with pentobarbital sodium (50 mg/kg IP) and injected intraperitoneally with heparin. A segment of abdominal aorta was excised, cut into rings 2–3 mm in length, threaded with dental wire and mounted in a 5 ml water jacketed organ chamber filled with modified Krebs solution (MKS) and gassed with 93% $O_2$, 7% $CO_2$ at 37° C. (Malis, C. D., Leaf, A., Varadarajan, G. S., Newell, J. B., Weber, P. C., Force, T. G., Bonventre, J. V., *Circulation* 84:1393–1401 (1991)). Thoracotomy was then performed and rings from the large extrapulmonary right and left branches of the main pulmonary artery (PA) were dissected free and mounted as for the aorta in a parallel tissue chamber. Oxygen and $CO_2$ tensions and pH were checked systematically by using a pH/blood gas analyzer. The functional status of the endothelium in aortic and pulmonary artery rings was determined by demonstrating acetylcholine-induced relaxation.

B. Experimental Protocol

HIF was prepared as described above in Example I. One unit of HIF in the vessel studies is defined as that amount of inhibitor that inhibits ouabain-sensitive $K^+$ transport by 50%, as determined by $^{86}Rb^+$ uptake into human erythrocytes (Carilli, C. T., Berne, M., Cantley, L. C., Haupert, G. T., Jr., *J Biol Chem* 260:1027–1031 (1985)). Because the molecular weights, and binding affinity of HIF and ouabain for purified $Na^+$, $K^+$-ATPase are similar (Haupert, G. T., Carilli, C., Cantley, L. C., *Am J Physiol* 247:F919–F924 (1984)), it can be estimated from the erythrocyte assay that 1 unit HIF is approximately 0.75 pmol ouabain-equivalent bioactivity. This estimate agrees very closely with earlier calculations that 1 unit/ 50 μl=15 nM HIF (Haupert, G. T., Carilli, C., Cantley, L. C., *Am J Physiol* 247:F919–F924 (1984)).

Baseline resting tension of vascular rings was set at 1.5 g based on maximal KCl-induced contractile response. Isometric force measurements were obtained with a Grassforce displacement transducer and continuously recorded. Pulmonary artery and aortic rings were studied simultaneously. Ring viability and contractile response was calibrated using KCl (5–25 mM). Rings were then washed free of KCl, equilibrated to stable baseline, and superfused with MKS containing HIF or ouabain. Wet weight of rings was obtained at the end of each experiment. The amplitude of contractions was measured as milligrams of tension above resting tension, percent change above resting tension, or change in tension in milligrams per milligram wet weight tissue. Data are expressed as means ±SEM. Analysis of variance followed by multiple comparison by the Fisher test for multiple comparisons were used to determine differences between groups. Paired Student's t tests were used where appropriate. Significance was assumed at p<0.05.

C. Effects of HIF of Resting Tension

HIF evoked a significantly greater contractile response in PA of hypertensive rats compared to normotensive rats. When normalized to the mean contractile response to a standard KCl concentration (15 mM), enhanced response in PA of SHR compared with SD remained highly significant (132±20% v. 35±6% of the KCl-stimulated tension, p<0.001).

The effect of HIF on PA was reversible and caused a cumulative concentration-dependent increase in tension in PA rings of hypertensive and normotensive rats, whereas approximately equimolar concentrations of ouabain did not. Ouabain in even much higher concentrations (4×10$^{-7}$M and 10$^{-4}$M) did not elicit contractions in PA rings consistent with the known resistance of rat $Na^+$, $K^+$-ATPase to ouabain. HIF-induced contractions were not altered in de-enothelialized aortic rings. HIF did not increase the sensitivity of PA rings to exogenous norepinephrine as contractile responses to different concentrations of norepinephrine ranging from 10$^{-9}$M to 10$^{-6}$M were identical before and after addition of HIF.

The effects of 20 U HIF (approximately 4 nM) on resting tension of pulmonary artery and aortic rings in SHR and SD are summarized in Table 5.

Whereas HIF constricted PA rings of hypertensive rats to a significantly greater extent than PA rings of normotensive rats, this difference was not observed in abdominal aortic rings (Table 5). In addition, for HIF-induced contractions, no significant difference was found between aortic and PA rings in normotensive animals, but in hypertensive rats the effect of HIF was significantly greater in PA compared to aortic rings (Table 5). This difference was not accounted for by a difference in vessel mass as change in tension normalized per milligram wet tissue weight was also significantly greater in PA rings compared with aortic rings (221±46 mg/mg wet wt vs. 108±19 mg/mg wet wt, respectively, p<0.05).

TABLE 5

HIF-induced change in tension (increase over resting tension) in various isolated vascular rings.

| Vessel | [HIF], nM | ΔTension (mg) | n | p |
|---|---|---|---|---|
| SHR PA | 4 | 308 ± 56 | 8 | <0.02 |
| S-D PA | 4 | 137 ± 26 | 8 | |
| SHR Ao | 4 | 145 ± 29 | 6 | =0.22 |
| S-D Ao | 4 | 93 ± 21 | 4 | |
| SHR PA | 4 | 308 ± 56 | 8 | <0.05 |
| SHR Ao | 4 | 145 ± 29 | 6 | |
| S-D PA | 4 | 137 ± 26 | 8 | =0.3 |
| S-D Ao | 4 | 93 ± 21 | 4 | |

SHR refers to spontaneously hypertensive rats; S-D refers to Sprague-Dawley rats; Ao refers to aortic rings; and PA refers to pulmonary artery rings; n is the number of vascular rings studied. Tension values are means ±SEM.

D. Pharmacological Interventions

Figure 5A:
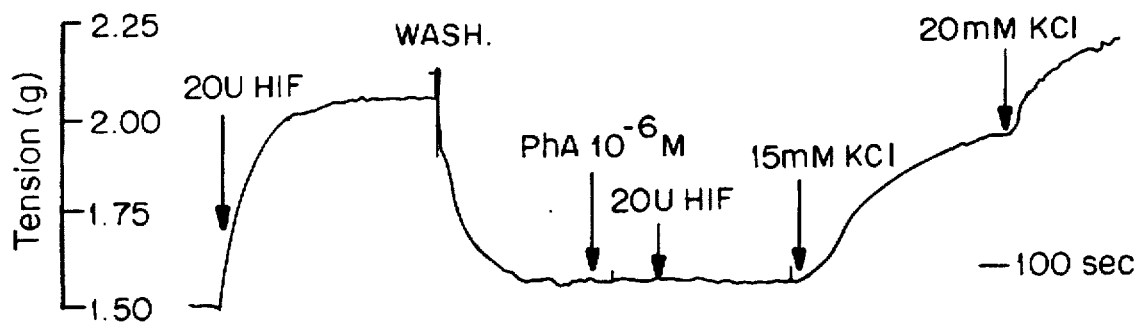
FIG. 5 is a graph plotting the effects of the alpha blocker phentolamine (PhA, $10^{-6}M$) (top) and nominal zero calcium (bottom) on HIF-induced constrictions of a representative vessel.
Figure 5B:
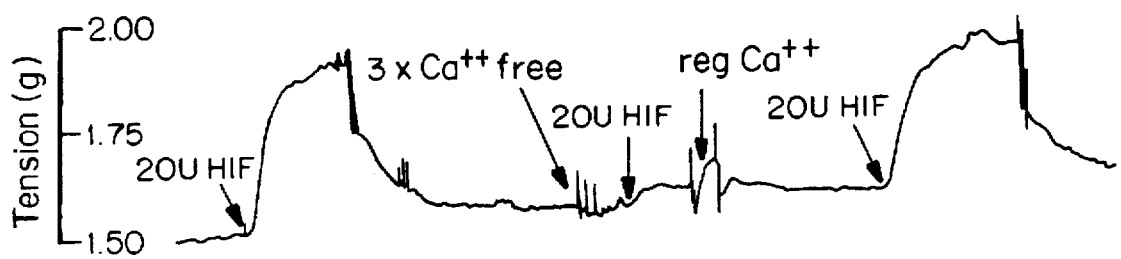

HIF-induced vasoconstriction in aortic and PA rings was completely abolished by 10$^{-6}$M phentolamine. FIG. 5 shows the effects of the alpha-blocker phentolamine (PhA, 10$^{-6}$M) (top), and nominal zero calcium (bottom) on HIF-induced constrictions of a representative vessel. At 2×10$^{-7}$M, the $Ca^{2+}$ channel blocker, verapamil, reduced the HIF-induced increase over resting tension by 35% (range 31% to 38%). However, 5×10$^{-8}$M verapamil, which exclusively blocks the $Ca^{2+}$ channels in PA without affecting alpha receptors, did not reduce the HIF-induced contraction.

HIF-induced increase in resting tension was dependent on extracellular $Ca^{2+}$. When $Ca^{2+}$ was omitted from the MKS in the tissue bath, almost no rise (<5%) over resting tension was observed with HIF (FIG. 5). When $Ca^{2+}$ was added back to the bath, tension promptly rose on retreatment with HIF.

Complete abolition of HIF-induced contractions in the presence of the alpha-receptor blocker phentolamine (1 μM) (FIG. 5), suggests that the contraction of the smooth muscles was due mainly to the action of norepinephrine. The exocytotic release of norepinephrine into the junctional cleft is normally triggered by $Ca^{2+}$ entry into the nerve terminal following the propagation of the action potential along the neuronal cell membrane. Norepinephrine release is therefore inhibited in a zero calcium milieu, a condition which also eliminated HIF-induced vasoconstriction (FIG. 5). Readdition of calcium to bathing medium containing HIF restored the vasoconstrictive response associated with HIF. HIF cannot be a catecholamine itself, since catecholamines produce initial vasocontrictions in zero $Ca^{2+}$ medium through direct stimulation of the alpha receptor and resulting release of $Ca^{2+}$ from intracellular stores. Furthermore, as described in Example VII, the structure of HIF is now known to be that of a glycosylated steroid lactone.

On the other hand, voltage dependent calcium channel blockage with verapamil (2×10$^{-7}$M) only caused a small decrease in HIF-induced tension development, and had no effect at all at lower doses (5×10$^{-8}$M). The latter concentration was shown in rabbit pulmonary artery to block transplasmalemmal $Ca^{2+}$ entry through voltage dependent calcium channels (Haeusler, G., *J Pharmacol Exp Ther* 180: 672–682 (1972)), but is a dose too low to produce partial alpha blockade that can occur with the larger verapamil dose we first used. These results indicate that depolarization of the vascular smooth muscle cell membrane with subsequent opening of calcium channels is not the likely mechanism by which HIF-induced sodium pump inhibition evokes the mechanical response in PA.

The results herein reported can be explained by considering that the release and reuptake of norepinephrine into sympathetic nerve terminals is coupled to neuronal $Na^+$ pump activity (Vanhoutte, P. M., Lorenz, R. R., *J Cardiovasc Pharmacol* 6:S88–S94 (1984)). $Na^+$, $K^+$-ATPase inhibitors block the neuronal uptake mechanism, and prevent post-junctional tissue accumulation of norepinephrine as shown by increased accumulation of tritiated norepinephrine in the junctional cleft following cardiac glycoside treatment (Flaim, S. F., DiPetti, D. J. *Am J Physiol* 236:613–619 (1979)). HIF-induced contractions may therefore result from increased concentrations of active neurotransmitter in the junctional cleft, with enhanced activation of postjunctional smooth muscle cell alpha-receptor sites. This concept fits with the long recognized role of the sympathetic nervous system in the genesis and/or maintenance of the hypertensive state in rat models of spontaneous hypertension. Indeed, many parameters of sympathetic function in blood vessels of hypertensive animals are changed, and chemical denervation with 6-hydroxydopamine can prevent or attenuate the development of hypertension (Hallback, M., Weiss, L. *Med Clin North Amer* 61:593–609 (1977)). In the SHR the $Na^+$, $K^+$-ATPase-coupled neuronal norepinephrine uptake process is activated, so that its efficacy in controlling the junctional concentration of norepinephrine is already enhanced (Vanhoutte, P. M., Verbeuren, T. J., Webb, R. C., *Physiol Rev* 61:151–247 (1981)). Interference with this local modulatory mechanism by an endogenous inhibitor might therefore be expected to have a more prominent pathophysiologic impact in spontaneously hypertensive rats than in the normotensive controls.

VII. Structural Analysis of HIF

Summary of Results:

Endogenous inhibitors of $Na^+$, $K^+$-ATPase have been isolated from mammalian sources and partially characterized by several laboratories. Recently, Mathews et al. (*Hypertension* 17:930–935 (1991)) reported that the factor they described was indistinguishable from ouabain based on HPLC coelution and mass spectrometric analyses. The mass spectroscopic methods employed, however, could not permit assignment of precise structure. Nonetheless, physiologic testing of the purified plasma inhibitor again gave results indistinguishable from ouabain (Bova, S., Blaustein, M. P., Ludens, J. H., Harris, D. W., DuCharme, D. W. and Hamlyn, J. M. *Hypertension* 17:930–935 (1991). In order to determine whether the comound described herein, bovine hypothalamic factor (HIF), is distinguishable from ouabain, sophisticated structural analyses were performed. To provide enough purified HIF to perform these analyses, an affinity purification procedure was developed that permitted a total of 2,200 units of HIF to be purified in several batches for structural analysis.

Using affinity chromatography and reversed phase HPLC as the penultimate and final purification steps, HIF was purified to homogeneity. Coinjection of acyl derivatives of ouabain and pure HIF showed that the two molecules had different retention times on HPLC, indicating a difference in structure. Differences in circular dichroism spectrometry of the penta- and hexa napthoyl derivatives of HIF and ouabain confirmed that there was difference in structure between these two compounds. Using the techniques of tandem mass spectrometry, circular dichroism spectrometry of acyl derivatives of HIF, gas chromatography-mass spectrometry and liquid chromatography-mass spectrometry of the cleaved sugar and steroid moieties, exact molecular mass and specific structural assignment became possible using submicrogram quantities of HIF. We report here that HIF is, like ouabain, an alpha L-rhamnoside, but differs from ouabain in its sugar-cardenolide arrangement, a change presumed to account for the observed differences in biological activity.

Affinity-purified HIF was found to be indistinguishable from ouabain in molecular mass. However the information generated by ion spray tandem mass spectrometry did not exclude the possibility that HIF is an isomer of ouabain. To address this uncertainty, ultramicrospectroscopic probes of affinity purified HIF were designed to unambiguously assign as much of the molecular structure possible given a limit of approximately one microgram of purified HIF as starting material. Two separate strategies were developed to analyze HIF: one to define the nature of the presumed sugar moiety; and the second to assign the stereo- and regio-chemistry of the intact glycoside and aglycone. In both cases, the experimental conditions were first established for authentic ouabain and then applied to both ouabain and HIF in a side by side comparison.

In the case of identifying the sugar subunit, analysis of HIF alongside ouabain on a 10 pmole per experiment scale has demonstrated the presence of rhamnose in both HIF and Ouabain. The intact glycosides were then analyzed on a larger scale (500 pmole) by derivatization, HPLC and circular dichroism (CD). The appearance of different derivatives for HIF and ouabain in this experiment provides the first chemical evidence that HIF is a structural isomer related to, but distinct from, ouabain. Because both HIF and ouabain are rhamnosides, the structural difference(s) could be due to a difference in the sugar stereochemistry, the position of glycosylation and/or the structure or stereochemistry of the aglycone of HIF as compared to ouabain.

A. Purification of HIF

Initial Purification: Initial purification of the $Na^+/K^+$-ATPase inhibitor was accomplished from bovine hypothalamus using aqueous/organic extractions, lipophilic gel chromatography, and cation and anion exchange chromatographies as previously described (Carilli, C. T., Berne, M., Cantley, L. C. and Haupert, G. T. Jr., *J. Biol. Chem.* 260:1027–1031 (1985)); Anner, B. M., Rey, H. G., Moosmayer, M., Meszoely, I., and Haupert, G. T. Jr., *Am. J. Physiol.* 258:F144–F153 (1990), and Example I above). Extracts purified to this point were free of proteins, lipids, vanadate and cations known to interfere in $Na^+/K^+$-ATPase bioassays. Dry residue after ion exchange was taken up in 10 ml of deionized water and applied to a 30 ml column of CHP20P resin (Mitsubishi) developed in water and eluted with a linear methanol gradient 0–100% pumped at 2 ml/min over 120 min. $Na^+/K^+$-ATPase inhibitory activity was monitored using ouabain- sensitive inhibition of $^{86}Rb^+$ uptake into human erythrocytes, inhibition of purified $Na^+/K^+$-ATPase, and inhibition of $^3H$-ouabain binding to a microsomal preparation of $Na^+/K^+$-ATPase as previously described (Haupert, G. T., Jr. and Sancho, J. M., *Proc. Natl. Acad. Sci. USA* 76:4658–4660 (1979); Haupert, G. T., Jr., Carrilli, C. T., and Cantley, L. C., *Am. J. Physiol.* 247:F919–F924 (1984); Carilli, C. T., Berne, M., Cantley, L. C. and Haupert, G. T., Jr., *J. Biol. Chem*, 260: 1027–1031 (1985)). Eluates of the CHP20P column contained two inhibitors of $Na^+/K^+$-ATPase activity, a non-specific, polar substance which eluted at 12 min, and HIF which eluted in a peak at 84 min. Residue in the HIF fraction was generally unweighable by microbalance, and yield of HIF after this step ranged from 150–750 pmol ouabain equivalent bioactivity/kg of starting tissue (1 unit of ouabain-equivalent bioactivity ~0.75 pmol HIF (Haupert, G. T., Jr., Carrilli, C. T., and Cantley, L. C., *Am. J. Physiol.* 247:F919–F924 (1984); Anner, B. M., Rey, H. G., Moosmayer, M., Meszoely, I., and Haupert, G. T., Jr., *Am. J. Physiol.* 258:F144–F153 (1990)), or 90–440 ng HIF/kg (see below).

Affinity Chromatography Purification of Partially Purified HIF:

The HIF was further purified by an affinity chromatography step which employed coupling of purified canine renal Na$^+$/K$^+$-ATPase (Haupert, G. T., Jr., Carrilli, C. T., and Cantley, L. C., *Am. J. Physiol.* 247:F919–F924 (1984)) to glutaraldehyde activated magnetic iron oxide particles having reactive primary amino groups (BioMag 4100, Advanced Magnetics, Cambridge, Mass.). Three ml of BioMag 4100 were activated with 5% glutaraldehyde following the manufacturers specifications. 4 mg of purified canine renal medullary Na$^+$/K$^+$-ATPase were agitated in coupling buffer overnight at 4° C. with the activated particles. Separation of particles from supernatants was done with a magnetic bar. Unreacted aldehyde groups were quenched with glycine. An aliquot of the magnetic particle-Na$^+$/K$^+$-ATPase complex was combined with CHP20P purified HIF (100 pmol HIF/2 mg ATPase) in the presence of a binding buffer consisting of 10 mM MgCl$_2$, 2 mM H$_3$PO$_4$, and 20 mM imidazole, pH 7.4 containing 250 mM sucrose and 1 mM EDTA. The mixture was agitated at room temperature for 3 hours. Binding of HIF to the batch column was documented by monitoring disappearance of HIF activity from the supernatant as measured with the coupled enzyme assay (Haupert, G. T., Jr., Carrilli, C. T., and Cantley, L. C., *Am. J. Physiol.* 247:F919–F924 (1984)). Binding efficiency was calculated by comparing supernatant HIF activity at T=0 min and T=180 min (T$_0$-T$_{180}$=HIF bound). At 3 h, binding buffer was separated from the column, and the particle-enzyme-HIF complex resuspended in an eluting buffer composed of 5 mM EDTA in 7.5 mM imidazole, pH 7.4. The eluting mixture was agitated overnight at 37° C., the supernatant separated from the column complex, and concentrated to dryness.

HPLC Chromatographic Purification of Affinity Purified HIF

Figure 6:
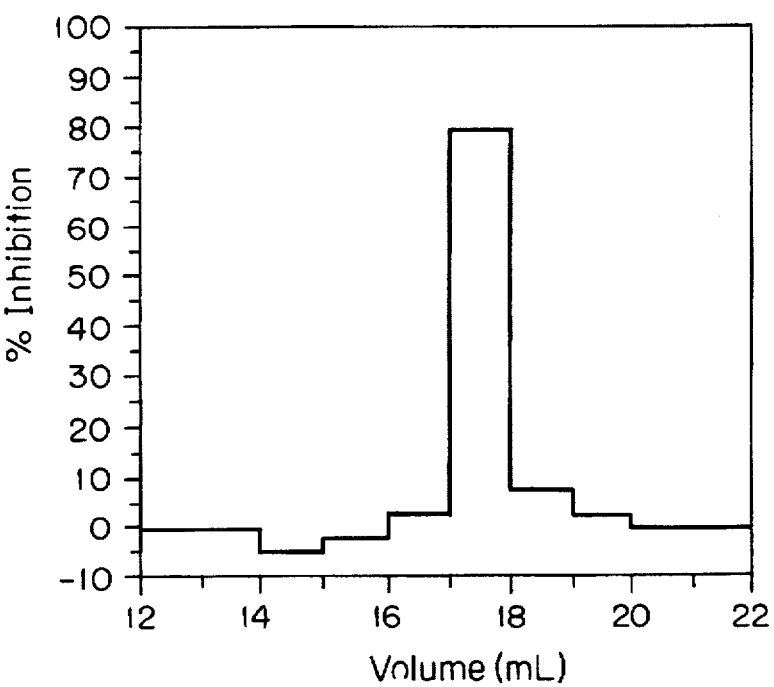
FIG. 6 shows the HPLC chromatogram of affinity purified HIF using a Waters Resolve RP C18 column.

Dried HIF was reconstituted in 250 µl of distilled water and injected onto a Waters Resolve RP C18 (8 mm×10 cm), flow rate 1 ml/min. A step gradient elution was employed: 100% H$_2$O:0%CH$_3$CN for 3 min, followed by a linear gradient which reached 87% H$_2$O:13% CH$_3$CN by 4 min and was continued at this mixture for 40 min. HIF activity eluted in a single peak at 18–21 min. Active fractions were pooled, assayed in the $^{86}$Rb$^+$ transport assay to calculate total units recovered, and rechromatographed. A representative HPLC chromatogram of rechromatographed affinity purified HIF is shown in FIG. 6. The fraction representing active sample was concentrated to dryness and stored under Argon gas at −70° C. until used in structure analysis experiments.

B. Ion Spray-Tandem Mass Spectrometry

Ion spray/tandem mass spectrometry of HIF indicated that it is indistinguishable from ouabain in mass. FIG. 7A and 7B show repeat analyses on 2 different preparations of HIF compared with ouabain. Only ions having an m/z of 602 are selected in the first quadrupole and only daughter ions having an m/z of 439 are selected in the third quadrupole. The detection of comparable ion intensity for HIF and ouabain as shown in FIGS. 7A and 7B indicates that the unknown sample must have an identical mass to ouabain as well as a daughter ion with the same mass as the steroid subunit of ouabain. The first two peaks shown in FIG. 7A indicate a strong signal intensity for ouabain (peak B) or ouabain spiked with acetonitrile from a side fraction from the HPLC purification of HIF (peak A). This fraction contains no active HIF but its presence with ouabain dampens the signal intensity when compared with ouabain alone. The positions marked C and D show the lack of signal given by injections of acetonitrile alone. Position E indicates the lack of signal given by the inactive side fraction used to dampen the ouabain signal in injection A. The active fraction of HIF gave a clear signal as shown by the repeat injections labelled at positions F and G. An additional inactive side fraction is shown at position H. FIG. 7B shows a repeat series of injections with a different preparation of HIF. Position A indicates ouabain. Position B is another inactive side fraction of acetonitrile from the HIF purification. Position C is HIF which is followed by an inactive side fraction labelled D. Position E indicates ouabain spiked with acetonitrile.

Methods:

Purified HIF or ouabain was ionized by injecting either 50 units of HIF or 5 ng of ouabain into a mobile phase of acetonitrile/H$_2$O containing 10 mM ammonium acetate. This chemical ionization procedure produces an (M+NH$_4$)$^+$ ion for ouabain having an m/z of 602. This ion is mass selected in the first quadrupole of a triple stage tandem mass spectrometer. This ion then undergoes collision with argon in the second quadrupole, resulting in a loss of the sugar moiety (as a neutral species) as well as a loss of ammonia. What remains is the steroid portion of ouabain with a positive charge having an m/z of 439. This ion is then mass selected in the third quadrupole and is the only ion detected. Dissolved samples were taken up in a 0.05 ml syringe and infused into the ionizing chamber at an infusion rate of 0.003 ml/min using a Harvard Apparatus syringe pump, model number 22. Spectra were acquired on a Sciex API III triple quadrupole mass spectrometer. The electrospray voltage was +4800. Zero grade air was used as the nebulization gas at a pressure of 40 psi.

C. Analysis of the Sugar Moiety of HIF:

The results of ion spray/tandem mass spectrometry analysis was consistent with HIF containing a sugar with a molecular mass identical to rhamnose. Using authentic ouabain as a model, conditions for microscale cleavage of ouabain to release rhamnose from the steroid were developed using both the enzyme naringinase (an α-L-rhamnosidase) and acid hydrolysis (Methods). The enzymatic cleavage experiments could be scaled down to the 10 pmol level by monitoring the extent of hydrolysis through bioassay of reaction mixture aliquots, since for both HIF and ouabain removal of the sugar moiety to produce the respective genins reduced biological activity by 100-fold in the $^{86}$Rb$^+$ assay (data not shown). Direct sugar analysis on the residual amount of enzymatically cleaved HIF was not possible due to a high background level of many sugars (including rhamnose) found in the commercial preparation of naringinase. Thus, another 10 pmol each of HIF and ouabain were hydrolyzed with HCl. Persilylation of these hydrolysates and analysis by GC/MS showed that both HIF and ouabain release rhamnose upon hydrolysis. The GC/MS retention times for perisylated sugars are shown in Table 6 below. It should be noted that several isobaric sugar derivatives (such as fucose, deoxyglucose and deoxygalactose) were easily resolved under the same GC/MS conditions.

The enzymatic hydrolysis experiments demonstrate that HIF contains rhamnose, but its identification as the D or L isomer could not be answered unambiguously, although the stereospecificity of most glycosidases supported the assignment of HIF as an α-L-rhamnoside. Definitive assignment of the isomeric form was therefore undertaken using chiral GC/MS analysis of the HIF-derived rhamnose. Tetratrifluoroacetates of sugars were prepared and analyzed for D and L rhamnose and acid hydrolysates of HIF (Methods). Table 7, below, shows retention times for the derivatized sugars. HIF hydrolysate and HIF hydrolysate spiked with L-rhamnose showed identical retention times and single peaks, while HIF hydrolysate spiked with D-rhamnose showed two peaks representing the L-rhamnose of HIF and the added D isomer. HIF is thus concluded to be an a-L-rhamnoside.

TABLE 6

GC/MS Retention Times for Persilylated Sugars

| Undervatized Sugar | Retention Time for Persilylated Product(s) (min) |
|---|---|
| L-rhamnose | 7:01 |
|  | 7:52 |
| L-fucose | 7:34 |
|  | 8:04 |
| 2-deoxy-D-galactose | 7:45 |
|  | 8:02 |
|  | 8:25 |
| 2-deoxy-D-glucose | 8:08 |
|  | 9:04 |
| guinovose | 8:27 |
|  | 9:13 |
| 2,5-anhydro-D-mannitol | 8:11 |
| Ouabain acid-hydrolysate | 7:00 |
|  | 7:53 |
| HIF acid-hydrolysate | 6:59 |
|  | 7:52 |

TABLE 7

Chiral GC/MS Analysis of Liberated Sugarts for HIF and Ouabain

| Sample | Retention time (min:sec) |
|---|---|
| Ouabain hydrolysate + authentic L-rhamnose | 6:15, single peak |
| HIF hydrolysate | 6:18 |
| HIF hydrolysate + L-rhamnose (first injection) | 6:17, single peak |
| HIF hydrolysate + L-rhamnose (second injection) | 6:19, single peak |
| HIF hydrolysate + D-rhamnose | 6:24 and 6:28 |

Methods:
Enzymatic Hydrolyses

Naringinase (Sigma N-1385) was dissolved to make a 2 mg/ml solution in 9:1 solution of 10 mM pyridinium acetate, pH 4.7/methanol. Subsamples (10 pmole per 50 µl of distilled water) of ouabain (Aldrich 14, 193-3) or affinity and HPLC-purified HIF were delivered into 100 µl microcentrifuge tubes. Naringinase solution (50 µl ) was added to start the reaction, then the tubes were sealed and incubated for 22 hours at 37° C. Aliquots for bioassay measurements were removed (10 µl per determination, duplicate determinations for T=0 and T=22 hours) and evaporated under vacuum. The dry samples were reconstituted in 50 µl of Rb assay buffer for analysis.

Acid Hydrolyses:

Subsamples (10 pmole each in distilled water) of ouabain (Aldrich 14, 193-3) or affinity and HPLC-purified HIF were delivered into 100 µl microconical glass vials and dried in a Speed Vac concentrator. The dried residues were redissolved in 50 µl of 2N sequanal grade HCl, heated at 110° C. for 5 minutes in a dry block and then chilled with ice. The acid was removed with a Speed Vac concentrator prior to derivatization.

Sugar Analysis:

Hydrolyzed samples or authentic sugar standards were prepared for analysis by reaction with 10 µl N-trimethylsilyl imidazole (Pierce 88623) at room temperature for 30 minutes. The resultant solution containing persilylated sugars was analyzed directly by gas chromatograph/mass spectroscopy (GC/MS) using a 30M DB-1 capillary column (J&W Scientific 122–1032), and using a splitless injection at 225° C. The column temperature was held at 120° C. for 1 minute, then a 16° C./min linear ramp was applied from 120° to 180° C. followed by a 5° C./min linear ramp from 180° to 250° C. The mass spectral measurements were performed using ammonia chemical ionization and monitoring m/z 470 & 380, $(M+NH_4)^+$ and $(M+NH_4)^+$—$(CH3)_3SiOH$ respectively (these ions are characteristic for the persilylated sugars isobaric with rhamnose). Gas chromatograph retention times, for both alpha and beta anomers of authentic sugar standards, were obtained from the summed ion current traces.

Chirality Determination

Authentic L-rhamnose, D-rhamnose and hydrolysates were prepared for analysis by reaction with a minimum volume of N-methyl-bis-trifluoroacetamide (Pierce 49700) and pyridine (1:1, 10 µl) at 60° C. for 30 minutes to form sugar tetrakistrifluoroacetates. Reaction mixtures were cooled and analyzed directly by chiral GC/MS using splitless injection (1 µl) onto a 25M Chirasil Val capillary column (Alltech 13636). The GC injector temperature was 175° C. and the column was held at 80° C. for 2 m, followed by a linear temperature gradient from 80° to 150° C. at 5° C./min. The mass spectral measurements were performed using methane chemical ionization and monitoring m/z 549 which corresponds to the $(M+H)^+$ ion for the tetrakistrifluoroacetate derivative of rhamnose. Chirality assignments were confirmed by coinjection with reference standards.

D. HPLC Separation and CD Spectroscopy of Naphthoylated HIF and Ouabain

With HIF and ouabain having both identical molecular mass and the same sugar moiety, structural difference to explain differences in biological activity were presumed to reside in the steroidal portion of the molecule. To further analyze the respective cardenolides the technique of circular dichroism spectroscopy of acylated derivatives was chosen since this method has been previously used to assign structure to natural products at the microgram level. Preliminary studies on authentic ouabain demonstrated that the choice of acylating reagents is critical. Naphthoylation of 0.3 µg of ouabain formed the pentanaphthoate as the sole product, yielding enough product after preparative HPLC to provide adequate signal for measurement of the CD spectrum.

Figure 8A:
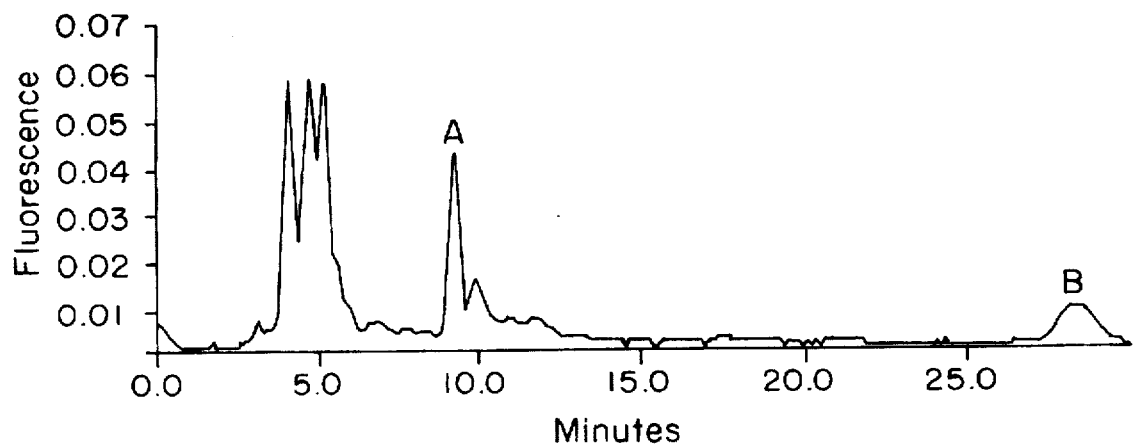
FIG. 8A shows the HPLC profile for the naphthoylation reaction yielding HIF pentanaphthoate (peak A) and HIF hexanaphthoate (peak B).
Figure 8B:
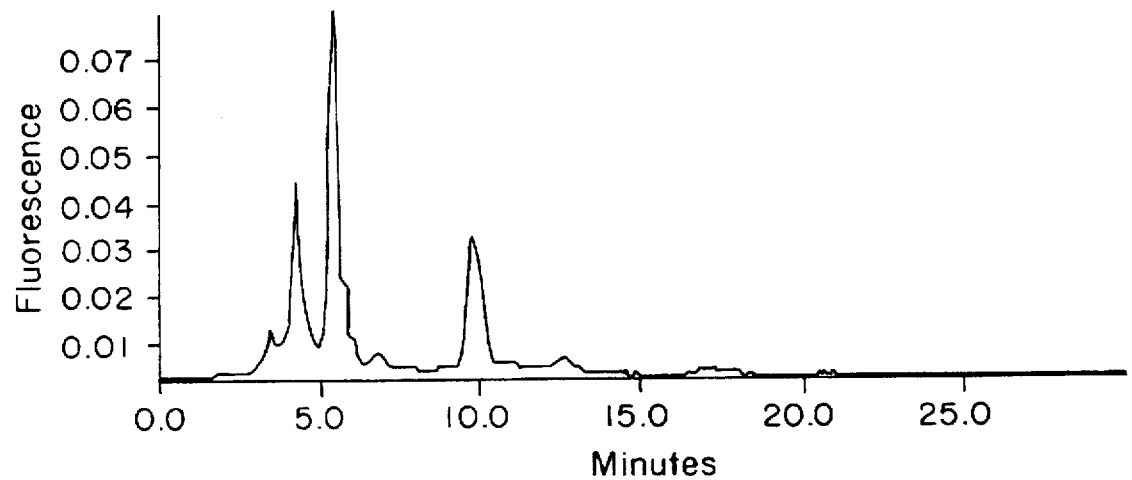
FIG. 8B shows the HPLC profile for ouabain pentanaphthoate.
Figure 8C:
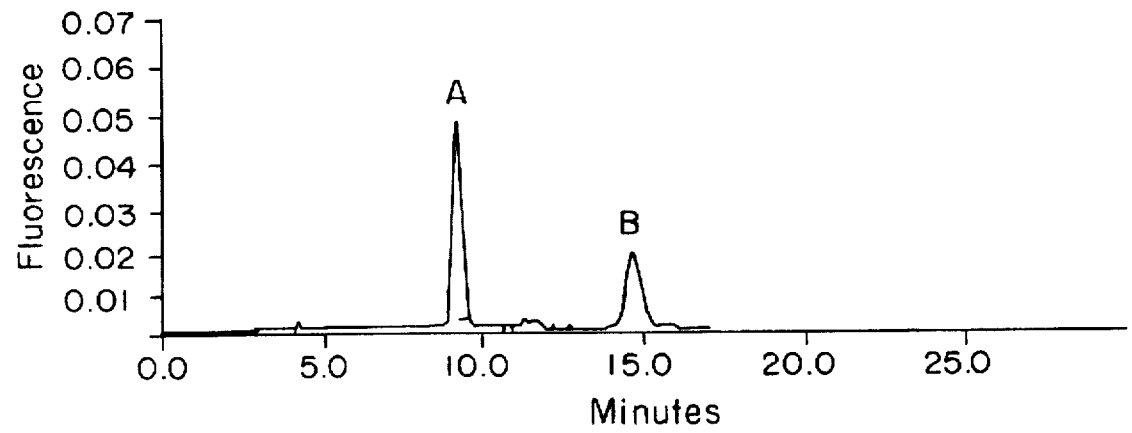
FIG. 8C shows the HPLC profile for ouabain pentanaphthoate (peak A) and ouabain hexanaphthoate (peak B).
Figure 9A:
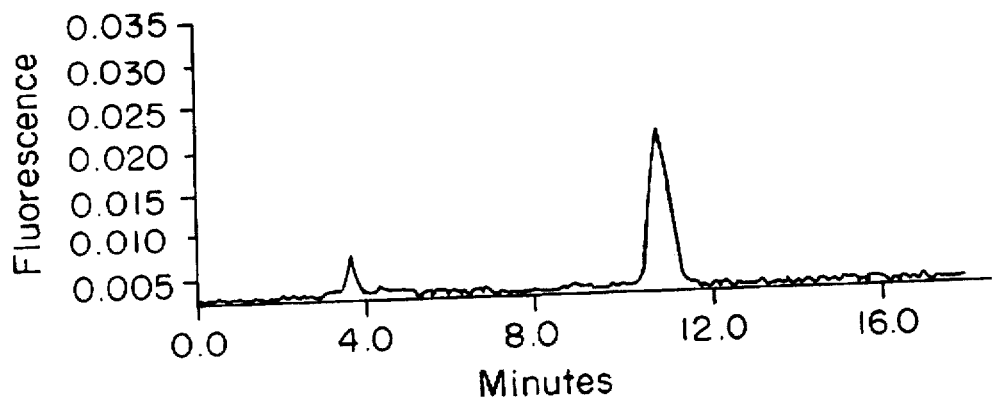
FIGS. 9A-9C compares the HPLC profiles of HIF and ouabain pentanaphthoates using a Vydac C18 HPLC column.
Figure 9B:
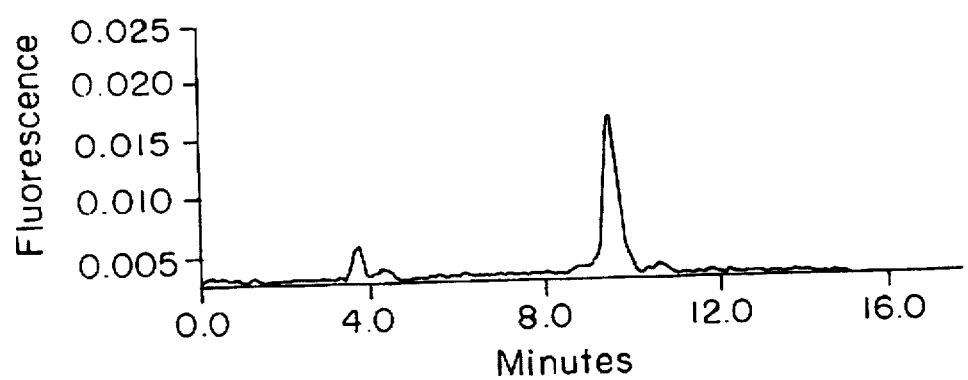
Figure 9C:
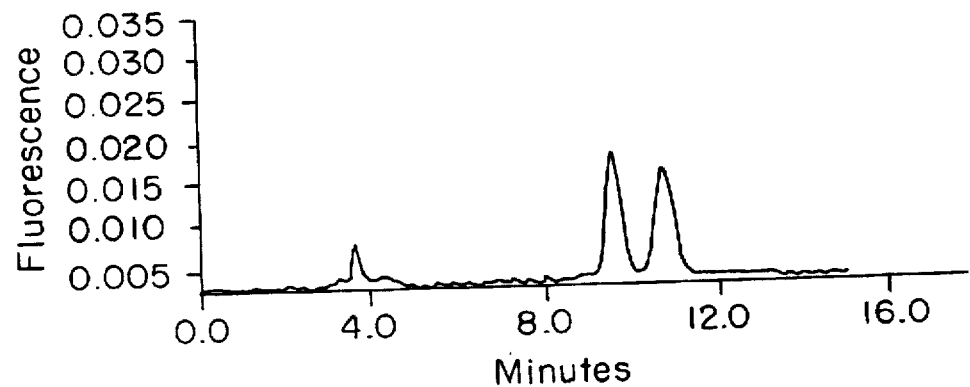
Figure 10A:
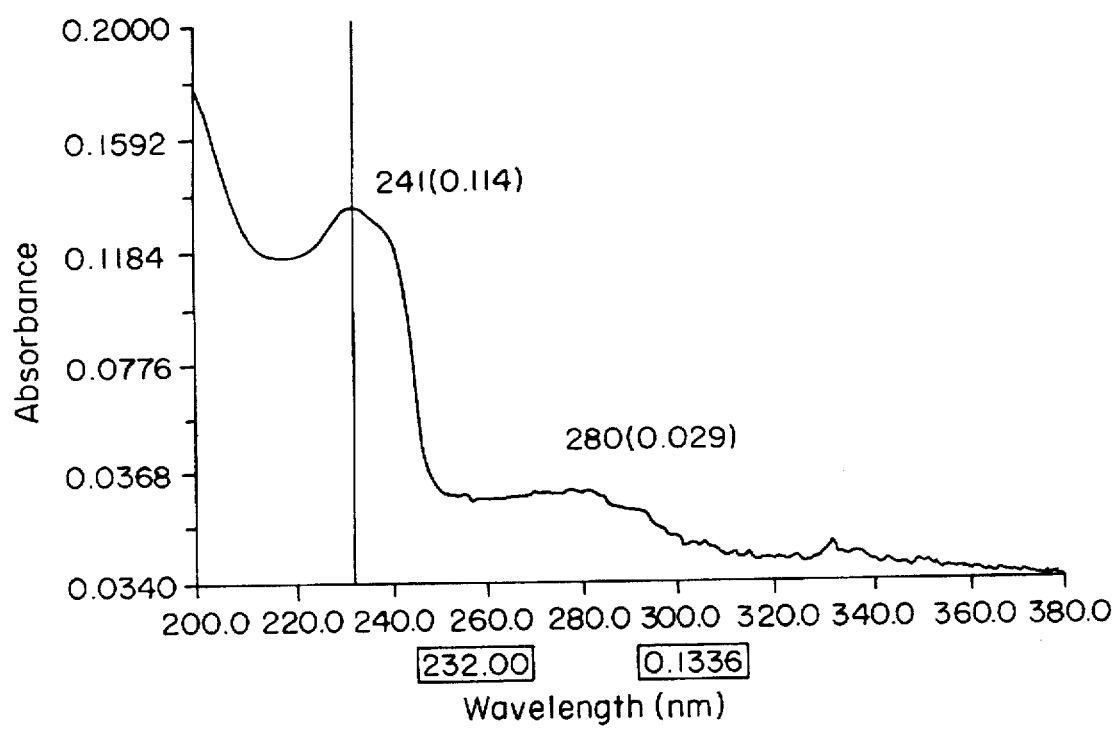
FIG. 10A shows the ultraviolet absorbance spectrum for HIF pentanaphthoate.
Figure 10B:
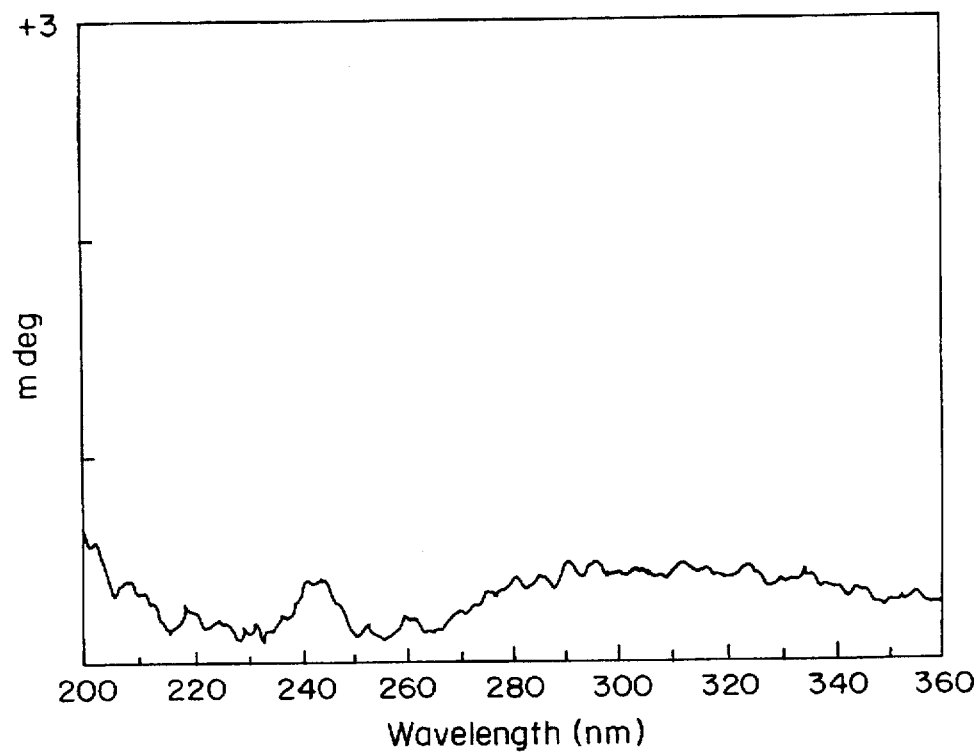
FIG. 10B shows the circular dichroism spectrum for HIF pentanaphthoate.
Figure 11A:
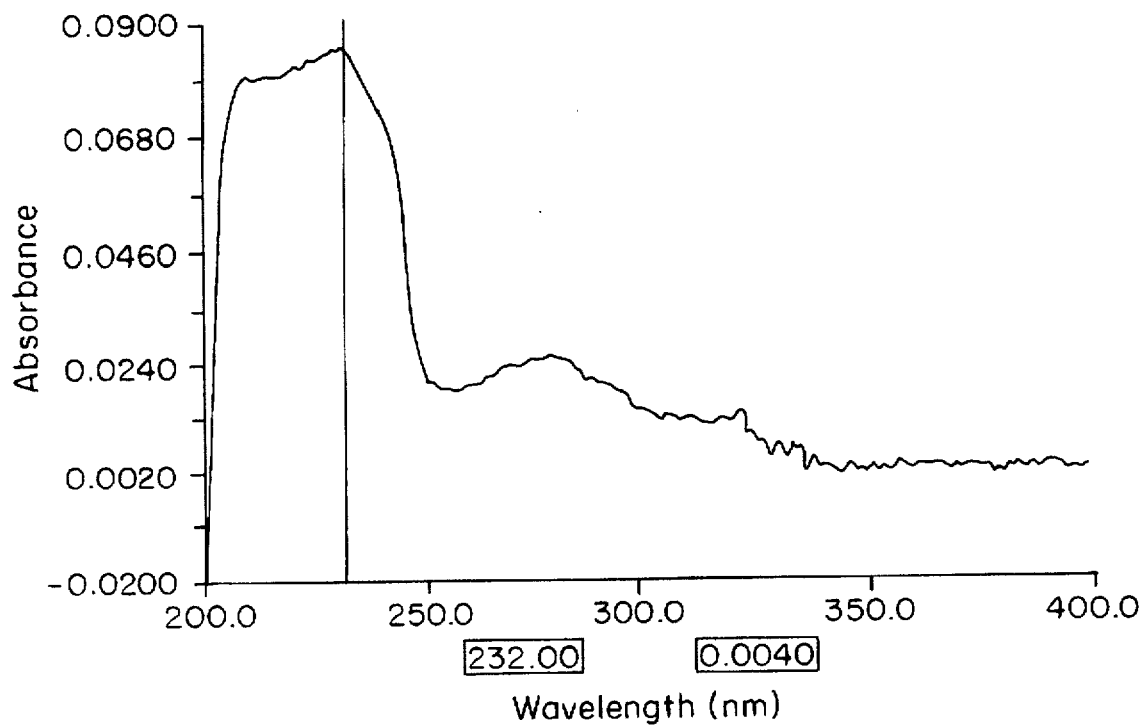
FIG. 11A shows the ultraviolet absorbance spectrum for ouabain pentanaphthoate.
Figure 11B:
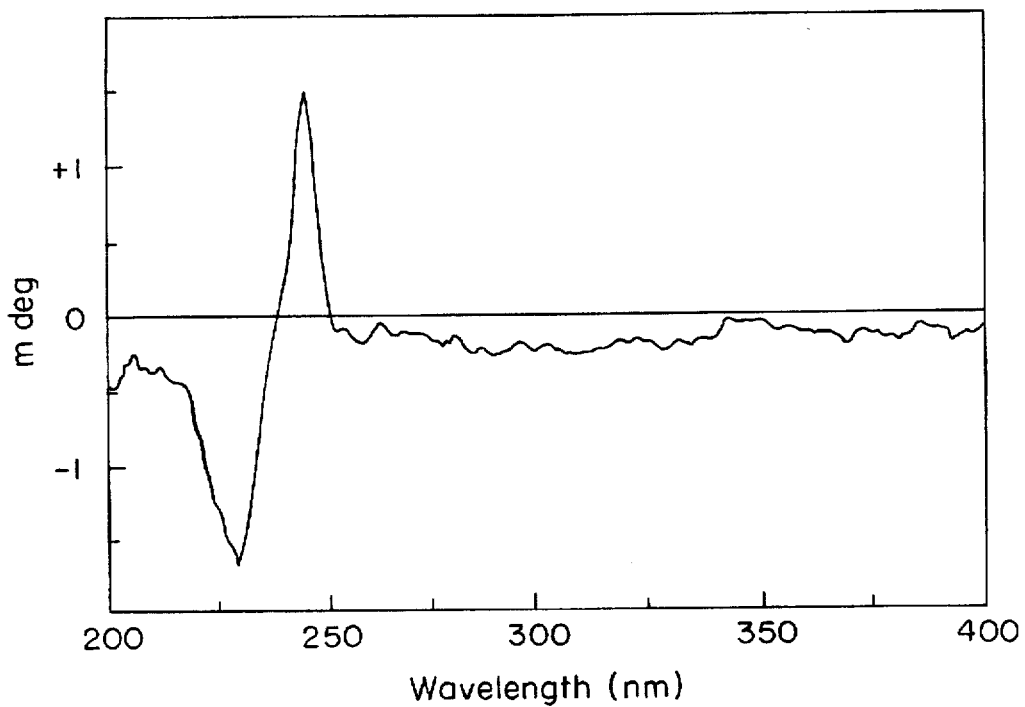
FIG. 11B shows the circular dichroism spectrum for ouabain pentanaphthoate.
Figure 12:
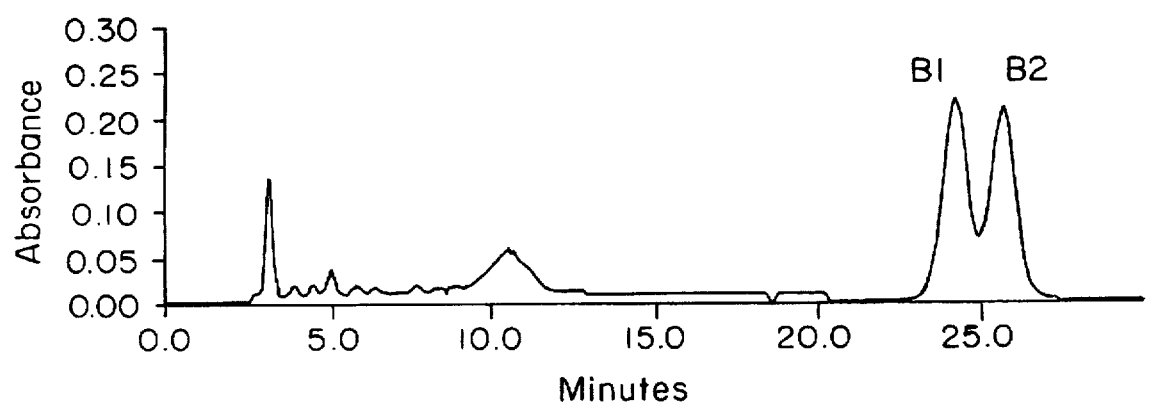
FIG. 12 shows further HPLC analysis of peak B from FIG. 8A above (representing HIF hexanaphthoate) using a Vydac C18 column.
Figure 13A:
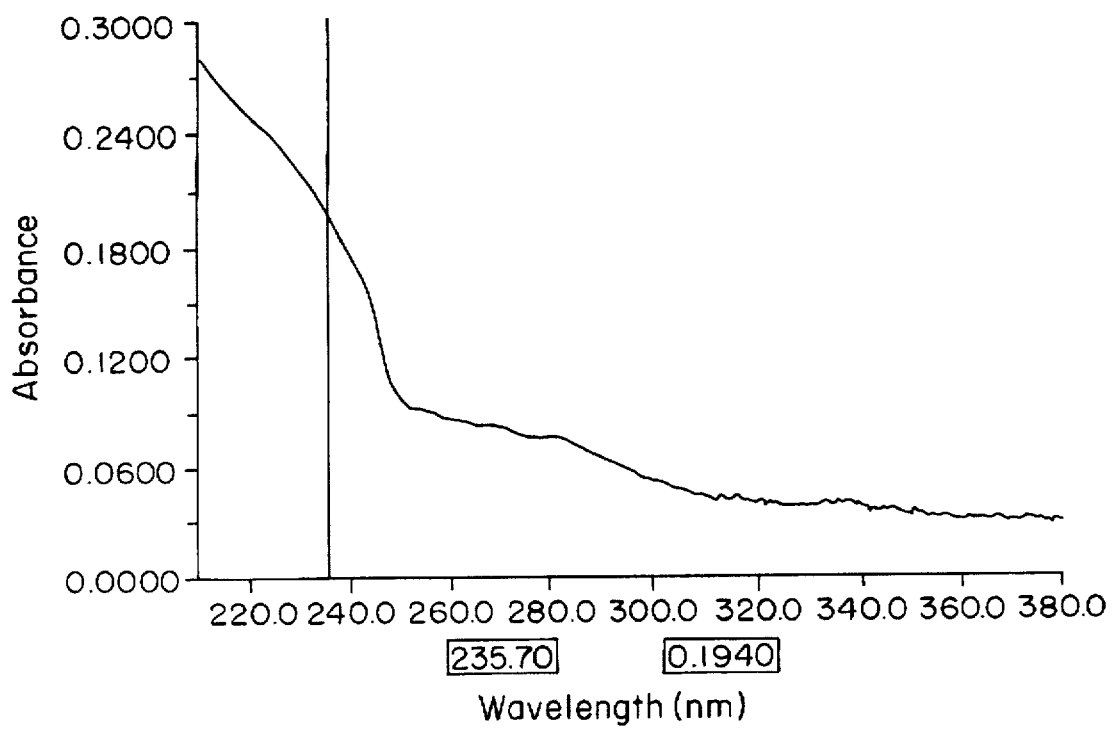
FIG. 13A shows the ultraviolet absorbance spectrum for peak B1 of the Vydac C18 profile of HIF hexanaphthoate.
Figure 13B:
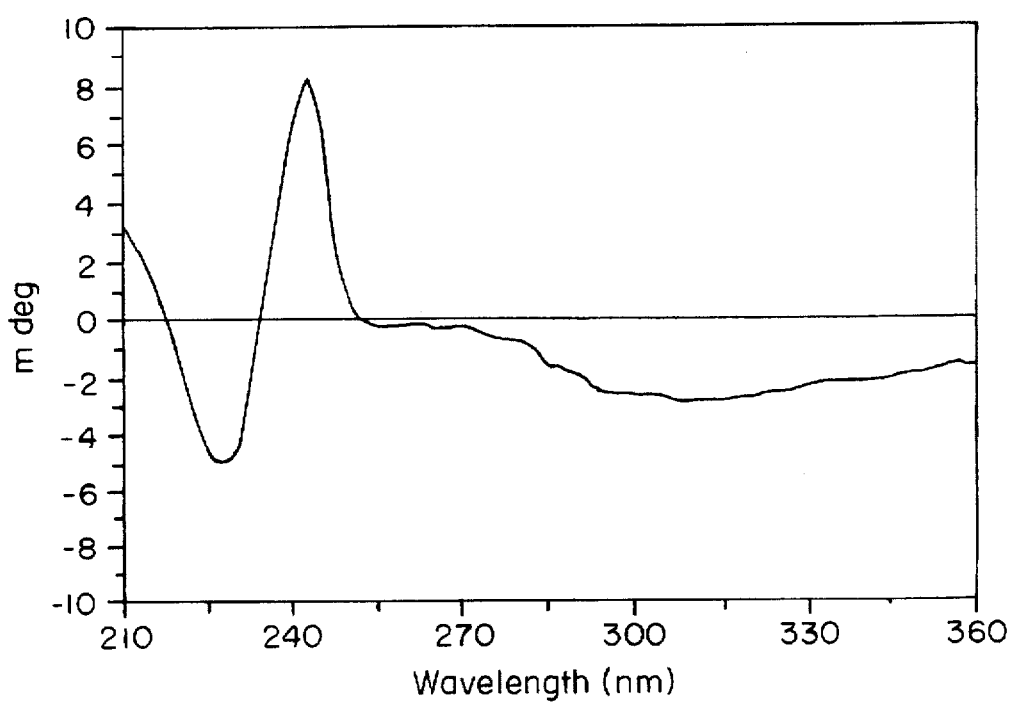
FIG. 13B shows the circular dichroism spectrum for peak B1 of the Vydac C18 profile of HIF hexanaphthoate.
Figure 14A:
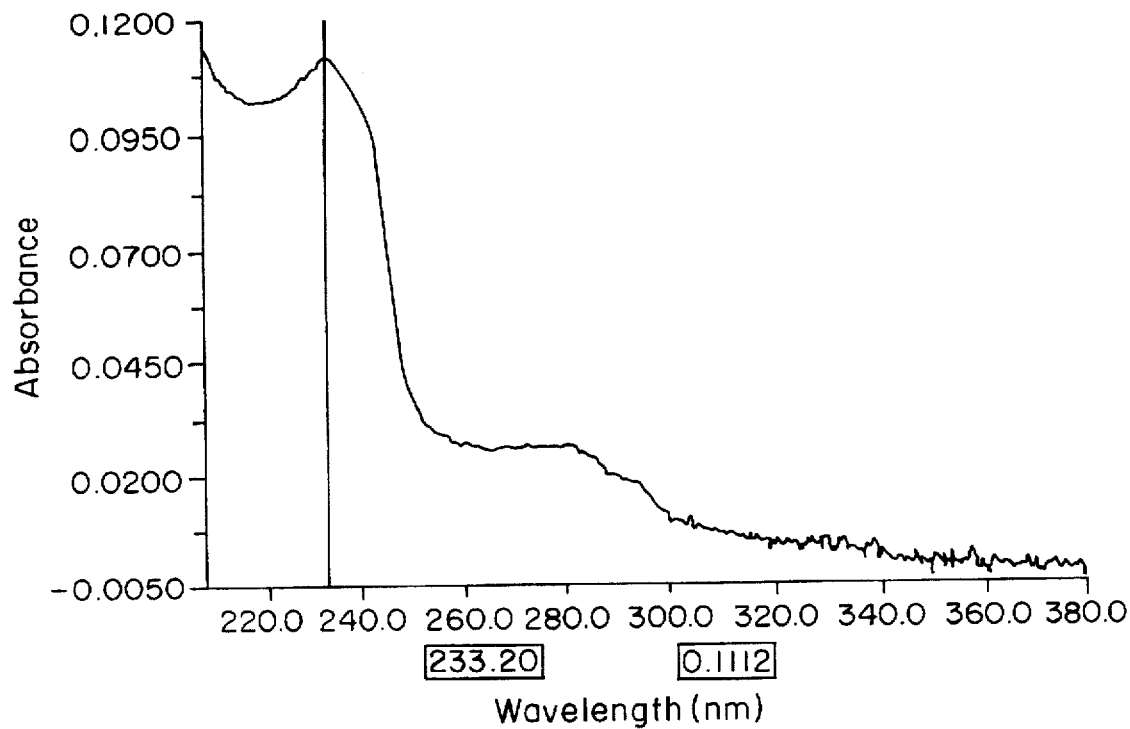
FIG. 14A shows the ultraviolet absorbance spectrum for peak B2 of the Vydac C18 profile of HIF hexanaphthoate.
Figure 14B:
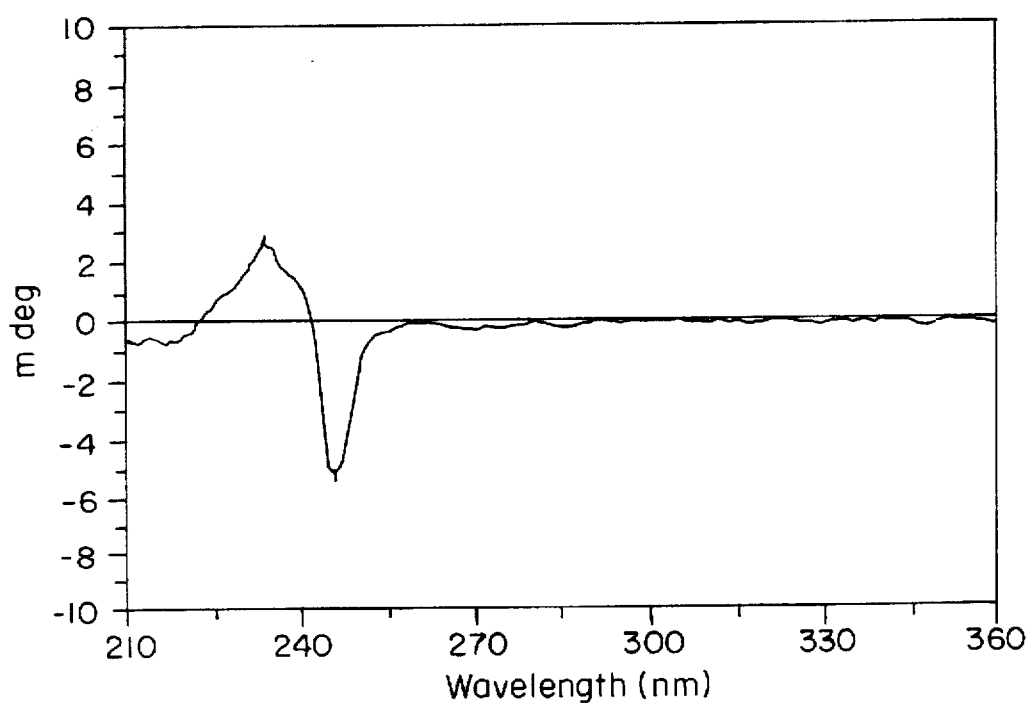
FIG. 14B shows the circular dichroism spectrum for peak B2 of the Vydac C18 profile of HIF hexanaphthoate.

Naphthoylations of ouabain and HIF were conducted side by side under the same conditions. Analysis of the reaction products by HPLC showed that ouabain formed exclusively one product, as expected (the pentanaphthoyl derivative, FIG. 8B), while HIF formed at least two products (FIG. 8A). Peak A derived from HIF showed a similar retention time as ouabain pentanaphthoate, while peak B derived from HIF is much more retained by RP HPLC than authentic ouabain hexanaphthoate (FIG. 8C). After preparative HPLC, the product in peak A (FIG. 8A) from the HIF naphthoylation reaction was shown to be distinct from ouabain pentanaphthoate by HPLC coelution (FIGS. 9A–9C). Although the mass spectrum of component A was weak, a potential parent ion was observed as well as fragment ions characteristic of ouabain pentanaphthoate (data not shown). Based on retention time (lipophilicity), UV and CD spectra, and mass spectral daughter ion for the sugar naphthoate, component A of HIF appears to be the pentanaphthoate, and component B, the hexanaphthoate of HIF. However the CD spectrum of component A (FIG. 10B) shows virtually no signal while a comparable amount of ouabain provides strong exciton coupling with a positive Cotton effect (FIG. 11B). FIGS. 10A and 11A show the corresponding ultraviolet absorbance spectra for HIF pentanaphthoate and ouabain pentanaphthoate, respectively. The more lipophilic product of the HIF naphthoylation reaction, peak B, was found to consist of two components (B1 and B2) after further HPLC analysis (FIG. 12). Based on the mass spectral fragments and lipophilicity, it is most likely that components B1 and B2 are alternative forms of hexanaphthoyl HIF. In the case of ouabain, the hexanaphthoate is expected to provide a weaker CD spectrum than the corresponding pentanapthoate (FIG. 11B). In contrast, the pentanaphthoate of HIF does not provide a strong CD spectrum (FIG. 10B) while the putative hexa derivatives of HIF allow exiton coupling to be observed. The CD spectra of B1 (FIG. 13B) and of B2 (FIG. 14B) were found to be of opposite sign, the former with a positive Cotton effect and the latter with a negative Cotton effect (FIGS. 13A and 14A show the ultraviolet absorbance spectra of peak B1 and B2, respectively, on the Vydac C18 profile of HIF hexanaphthoate). The HPLC and CD profiles of B1 and B2 are further proof that HIF and ouabain are structurally different.

E. Characterization of the Aglycone of HIF by LC/MS

Figure 15B:
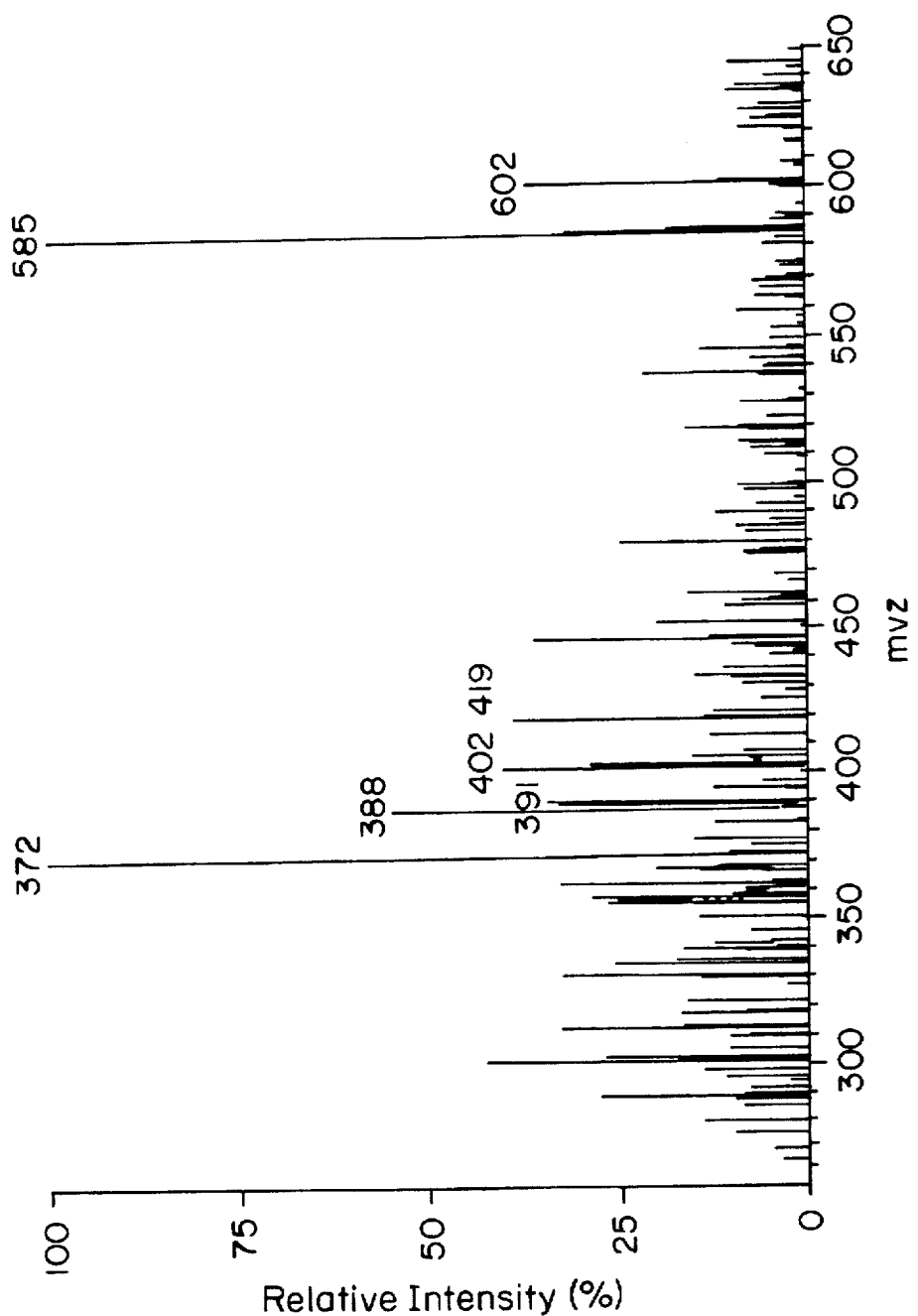
FIG. 15B shows the full scan mass spectra of intact HIF.

Side by side comparisons of naringinase-treated ouabain and HIF were carried out using full scan mass spectra and single ion monitoring chromatography of the respective hydrolysates. Single ion monitoring chromatograms of HIF hydrolysates showed ions of $R_t$ of 5.5 min. and 6.1 min. Full scan mass spectra at these respective retention times showed all expected ions for the aglycone of HIF and the holomolecule. Thus, at $R_t$=5.51 min., parent ions were observed at m/z 439+ and 456+, representing $(M+H)^+$ and $(M+NH4)^+$ ions of the HIF genin (FIG. 15A), and at $R_t$=6.78 min., parent ions were observed at 585+ and 602+, representing $(M+H)^+$ and $(M+NH4)^+$ ions of uncleaved HIF (FIG. 15B). Retention times for the HIF-genin and holo-HIF coincided exactly with side by side analysis of the $R_t$ for ouabagenin and authentic ouabain (data not shown). Since the full scan mass spectrum of HIF at a $R_t$ coincident with reference ouabain was indistinguishable from ouabain, there is no evidence that HIF contains more than one sugar subunit.

Thus, in addition to containing L-rhamnose in an α glycosidic linkage, the aglycone of HIF is confirmed to have the same molecular mass as ouabagenin with an identical retention time on HPLC. This result indicates a remarkable similarity in the stereochemistry of the genins of HIF and ouabain, even though the two holomolecules are shown to be non-identical by HPLC resolution and CD spectral analysis of acyl derivatives. These results indicate that HIF differs from ouabain as a subtle isomer in the steroid backbone, or as an isomer in the glycosidic linkage.

Methods:

Naphthoylation:

Each sample (ca. 500 pmole in a silylated, conical vial) was dissolved in 250 μl of anhydrous acetonitrile, then 1.5 mg of naphthoylimidazole and 0.4 μl of 1,8-diazabicyclo [5.4.0.]undec-7-ene (DBU) were added. The reactions were stirred at room temperature for 3 hours and then quenched by adding 1 ml of 20% aqueous acetonitrile. Reaction mixtures were loaded onto C18 Sep Pak (Waters, Millipore Corp.) cartridges and washed sequentially with 2 ml of 20% acetonitrile, 8 ml of 40% acetonitrile, 5 ml of 50% acetonitrile and finally with 5 ml of acetonitrile. The last washing was collected and subjected to HPLC analysis.

HPLC of Napthoylation Products:

Preparative chromatography was performed on a Phenomenex C18 column (4.6×250 mm, 10 μm) with isocratic elution using MeOH/$H_2$O 92:8 with a Perkin-Elmer Series 4 chromatograph delivering a flow of 1 ml/min. The column was monitored using a Shimazu RF-551 fluorescence detector with excitation at 234 nm and emission monitoring at 374 nm. For coelution experiments of the pentanaphthoates, a Vydac C18 column (4.6×250 mm) was employed with isocratic acetonitrile/water 83:17 at a flow of 1 ml/min. The Vydac column with acetonitrile/water 82:18 at a flow of 1 ml/min was used or preparative separation of component B1 from B2.

CD Spectroscopy:

CD spectra were obtained on a JASCO J-720 spectropolarimeter using acetonitrile as solvent. A microcell attachment was employed as necessary.

Liquid Chromatograph/Mass Spectroscopy of Hydrolyzed HIF and Ouabain

Samples were dissolved in 10 mM pyridinium acetate, pH 4.7-methanol (9:1), and injected onto a PLRP-S column (4.4×150 mm, Polymer Laboratories, Amherst, Mass.). The column was eluted with a 1 ml/min linear gradient from 90:10 to 80:20 of 2 mM ammonium acetate-acetonitrile using a Waters 600 MS HPLC. The HPLC effluent was connected to the LC/MS interface of a Sciex API III mass spectrometer (Thornhill, Ontario, Canada) where the flow was split 20:1 reducing the flow into the ionspray source to 50 μl/min. The mass spectrometer was scanned from 350 to 1000 daltons in 2.8 s.

Equivalents

Those skilled in the art will recognize, or be able to ascertain using no more than routine experimentation, numerous equivalents to the specific embodiments of the invention described specifically herein. Such equivalents are intended to be encompassed in the scope of the following claims.

I claim:

1. A method for producing a positive inotropic effect in a mammalian host by administering to the host a positive inotropic effect-producing amount of a glycosidic Hypothalamic Inhibitory Factor, wherein said Factor has been purified to homogeneity.

2. A method for treating cardiac malfunction in a mammal suffering therefrom by administering a positive inotropic effect-producing amount of a glycosidic Hypothalamic Inhibitory Factor to said mammal, said Hypothalamic Inhibitory Factor specifically binding sodium, potassium-AtPase reversibly and with high affinity wherein said Factor has been purified to homogeneity.

3. A method of claim 2 in which the cardiac malfunction is congestive heart failure, paroxysmal atrial tachycardia or atrial fibrillation.

4. A method of treating a mammal with cardiac glycoside intoxication comprising administering to the mammal a therapeutically effective amount of a glycosidic Hypothalamic Inhibitory Factor, wherein said Factor has been purified to homogeneity, to treat said cardiac glycoside intoxication and a therapeutically acceptable carrier.

5. A method for treating a mammal with an edematous disorder comprising administering a therapeutically effective amount of a glycosidic Hypothalamic Inhibitory Factor, wherein said Factor has been purified to homogeneity, to the mammal.

6. A method of claim 5 in which the edematous disorder is congestive heart failure, cirrhosis of the liver or nephrotic syndrome.

7. A method of treating a mammal with hypertension comprising administering to the mammal an analogue of a glycosidic Hypothalamic Inhibitory Factor, wherein said Factor has been purified to homogeneity, to prevent or modulate the binding of native Hypothalamic Inhibitory Factor.

8. A method of treating a mammal with hypotension comprising administering to the mammal a therapeutically effective amount of a glycosidic Hypothalamic Inhibitory Factor, wherein said Factor has been purified to homogeneity.

* * * * *